US010849551B2

(12) United States Patent
Delport

(10) Patent No.: US 10,849,551 B2
(45) Date of Patent: Dec. 1, 2020

(54) INTEGRATED LIGAMENT STRAIN MEASUREMENT

(71) Applicant: Surgical Sensors BVBA, Sint-Niklaas (BE)

(72) Inventor: Hendrik Delport, Sint-Niklaas (BE)

(73) Assignee: Surgical Sensors BVBA, Sint-Niklaas (BE)

(*) Notice: Subject to any disclaimer, the term of this patent is extended or adjusted under 35 U.S.C. 154(b) by 0 days.

(21) Appl. No.: 16/311,769

(22) PCT Filed: Dec. 27, 2016

(86) PCT No.: PCT/EP2016/082732
§ 371 (c)(1),
(2) Date: Dec. 20, 2018

(87) PCT Pub. No.: WO2017/220173
PCT Pub. Date: Dec. 28, 2017

(65) Prior Publication Data
US 2019/0209079 A1 Jul. 11, 2019

Related U.S. Application Data

(60) Provisional application No. 62/354,429, filed on Jun. 24, 2016.

(30) Foreign Application Priority Data
Jun. 24, 2016 (EP) .................................. 16176112

(51) Int. Cl.
*A61B 5/00* (2006.01)
*G01R 33/07* (2006.01)
(Continued)

(52) U.S. Cl.
CPC .......... *A61B 5/4533* (2013.01); *A61B 5/0031* (2013.01); *A61B 5/686* (2013.01);
(Continued)

(58) Field of Classification Search
CPC ..... A61B 5/0031; A61B 5/4533; A61B 8/485; A61B 90/06; A61B 2090/061;
(Continued)

(56) References Cited

U.S. PATENT DOCUMENTS 3,332,009 A 7/1967 Seale
4,813,435 A * 3/1989 Arms ................... A61B 5/1107
600/587

(Continued)

FOREIGN PATENT DOCUMENTS

EP 2110077 A1 10/2009
EP 2559386 A1 2/2013
(Continued)

OTHER PUBLICATIONS

B. Beynnon et al.; "The measurement of anterior cruciate ligament strain in vivo"; International Orthopaedics, vol. 16, No. 1, Mar. 1, 1992, pp. 1-12.
(Continued)

*Primary Examiner* — Larry E Waggle, Jr.
(74) *Attorney, Agent, or Firm* — James Creighton Wray

(57) ABSTRACT

The current invention relates to an integrated device suitable for measuring the difference between a strain in a ligament at a first point in time and said strain at a second point in time, said integrated device comprising: a ligament-attaching element adapted to be fastened on said ligament; a slider module adapted to be fastened on said ligament near said first ligament-attaching element, said slider module comprising a slider guiding channel; a slider comprising a distal slider end and a proximal slider end, said distal slider end
(Continued)

fastened on said ligament-attaching element, said proximal slider end guided in said slider guiding channel; a sensor configured to measure a strain-indicating parameter representing a position of said proximal slider end for obtaining said difference between said strain in said ligament at said first point in time and said strain at said second point in time, wherein said sensor comprises a Hall sensor which converts a position of said proximal slider end into a conditioned electrical signal carrying said measurement of said strain-indicating parameter.

16 Claims, 11 Drawing Sheets

(51) Int. Cl.
*A61B 90/00* (2016.01)
*A61F 2/46* (2006.01)

(52) U.S. Cl.
CPC .......... *A61B 5/7425* (2013.01); *A61B 90/06* (2016.02); *A61F 2/4657* (2013.01); *G01R 33/072* (2013.01); *A61B 2090/061* (2016.02); *A61B 2562/0261* (2013.01); *A61F 2002/4658* (2013.01); *A61F 2002/4666* (2013.01)

(58) Field of Classification Search
CPC .......... A61B 2562/0261; A61F 2/4657; A61F 2002/4658
See application file for complete search history.

(56) References Cited

U.S. PATENT DOCUMENTS

| 4,964,862 | A | 10/1990 | Arms |
| 5,540,696 | A | 7/1996 | Booth, Jr. |
| 5,597,379 | A | 1/1997 | Haines |
| 5,713,897 | A | 2/1998 | Goble |
| 5,733,292 | A | 3/1998 | Gustilo |
| 5,777,467 | A | 7/1998 | Arms |
| 5,800,438 | A | 9/1998 | Tuke |
| 5,860,980 | A | 1/1999 | Axelson, Jr. |
| 5,911,723 | A | 6/1999 | Ashby |
| 6,022,377 | A | 2/2000 | Nuelle |
| 6,575,980 | B1 | 6/2003 | Robie |
| 7,604,629 | B2 * | 10/2009 | Gerber ................ A61B 5/0031 604/891.1 |
| 8,078,440 | B2 | 12/2011 | Otto |
| 8,211,041 | B2 | 7/2012 | Fisher |
| 8,491,589 | B2 | 7/2013 | Fisher |
| 2003/0187452 | A1 | 10/2003 | Smith |
| 2011/0213221 | A1 * | 9/2011 | Roche ................ A61B 5/0031 600/301 |
| 2013/0217998 | A1 | 8/2013 | Mahfouz |
| 2015/0238204 | A1 | 8/2015 | Stone |
| 2015/0374984 | A1 * | 12/2015 | King .................... A61N 1/0468 607/50 |

FOREIGN PATENT DOCUMENTS

| WO | WO-9811816 A1 * | 3/1998 | ......... A61B 1/00156 |
| WO | 2012082628 A1 | 6/2012 | |

OTHER PUBLICATIONS

B.C. Fleming et al.; "An in vivo comparison of anterior tibial translation and strain in the anteromedial band of the anterior cruciate ligament"; Journal of Biomechanics, Pergamon Press, New York, NY, US; vol. 26, No. 1; Jan. 1, 1993, pp. 51-58.

M.H. Pope et al.; "Effect of knee musculature on anterior cruciate ligament strain in vivo"; Journal of Electromyography and Kinesiology, Elsevier, Amsterdam, NL; vol. 1, No. 3; Sep. 1, 1991, pp. 191-198.

* cited by examiner

INTEGRATED LIGAMENT STRAIN MEASUREMENT

This application claims the benefit of European Application No. 16176112.7 filed Jun. 24, 2016, U.S. Provisional Application 62/354,429 filed Jun. 24, 2016 and PCT/EP2016/082732 filed Dec. 27, 2016, International Publication No. WO 2017/220173 A1, which are hereby incorporated by reference in their entirety as if fully set forth herein.

TECHNICAL FIELD

The invention pertains to the technical field of medical/surgical devices, systems and methods. More specifically, the invention relates to devices, systems and methods for enhancing a surgery procedure such as a knee surgery procedure.

BACKGROUND

Total knee replacement surgery, also referred to as total knee arthroplasty (TKA), is becoming an increasingly important treatment for chronic knee pain and joint dysfunction. Techniques for placing artificial knee prostheses should be optimized to provide high chance of a good outcome and reduce wear of the prostheses, to thus reduce the need for repeated TKA surgeries. Improved techniques and devices are therefore useful for all TKA patients, with better functioning of the knee joint and longer useful life of the prosthetic knee. Similarly, other types of surgery such as Total Hip Artroplasty (THA), fractures with osteosynthesis and other treatments involving ligaments, tendons, bones, fasciae or capsules may benefit from improved techniques and devices.

The knee is generally defined as the point of articulation of the femur with the tibia. Structures that make up the knee include the distal femur, the proximal tibia, the patella, and the soft tissues within and surrounding the knee joint. Four ligaments are especially important in the functioning of the knee—the anterior cruciate ligament, the posterior cruciate ligament, the medial collateral ligament (MCL), and the lateral collateral ligament (LCL). In an arthritic knee, protective cartilage at the point of articulation of the femur with the tibia has been worn away to allow the femur to directly contact the tibia. This bone-on-bone contact causes significant pain and discomfort. The primary goals of a TKA procedure are to replace the distal end of the femur, the proximal end of the tibia, and often the inner surface of the patella with prosthetic parts to avoid bone-on-bone contact and provide smooth, well-aligned surfaces for joint movement, while also creating a stable knee joint that moves through a wide range of motion.

One of the greatest problems in TKA surgery is the impact on ligaments, especially the medial and lateral collateral ligaments. The collateral ligaments, which connect the distal femur and proximal tibia on the medial and lateral aspects of the knee, account for much of the stability and movement of the knee. If one of the collateral ligaments is too lax or too tight relative to the other collateral ligament, the knee will typically be unstable, range of motion may be limited, the patella may track improperly, and the femur and/or tibia may wear unevenly, leading to arthritis and pain. Uneven ligament tension after TKA surgery will typically cause joint instability and poor patellar tracking, limited range of motion, and impaired function of the knee, as well as uneven, increased wear of the prosthetic device, which often necessitates repeat surgery. Thus, it is imperative for the short- and long-term success of a TKA procedure to achieve balanced ligament tension in the knee through a full range of motion.

Many articles and studies have been devoted to ligament tension in the context of TKA, such as the following: Kurtz, S et al., "Projections of primary and revision hip and knee arthroplasty in the United States from 2005 to 2030," J. Bone Joint Surg. Am., Vol. 89, 2007, 780-785; Bourne, R B et al., "Patient satisfaction after total knee arthroplasty: who is satisfied and who is not?" Clin. Orthop. Rel. Res., Vol. 468, 2010, 57-63; Dunbar, M J et al., "I can't get no satisfaction after my total knee replacement: rhymes and reasons," Bone Joint J., Vol. 95-B, 148-152, 2013; Baker, P et al., "The role of pain and function in patient satisfaction after TKA," J. Bone Joint Surg., Vol. 89-B, 2007, 893-900; Delport, HP, Vander Sloten, J, Bellemans, J, "New possible pathways in improving outcome and patient satisfaction after TKA," Acta Orthop. Belg., Vol. 79, 2013, 250-254; Delport, HP, Labey, L, De Corte, R, Innocenti, B, Vander Sloten, J, Bellemans, J, "Collateral ligament strains during knee joint laxity evaluation before and after TKA," Clin. Biomech., Vol. 28, 2013, 777-782; Delport, HP, Labey, L, De Corte, R, Innocenti, B, Vander Sloten, J, Bellemans, J, "Restoration of constitutional alignment in TKA leads to more physiological strains in the collateral ligaments," Knee Surg. Sports Traumatol. Arthroscopy, Vol. 23(8), 2014, 2159-2169; and Delport, HP, "Collateral Ligament Strain of the Human Knee Joint. Native and after Total Knee Arthroplasty. The Importance of the Soft Tissue Envelope," PhD dissertation, KU Leuven, 2013. These documents concern research on ligament tension before and after TKA, said research being limited to research on cadavers.

One technique for reducing collateral ligament tension during a TKA procedure involves cutting fibers of one or both ligaments to decrease ligament tension—a technique referred to as "ligament release." Although ligament release is still commonly used, the disadvantage of this technique is that it requires actually cutting ligament tissue, thus weakening the ligament(s) and leaving less room for error if future releases or TKA procedures are required.

A number of devices and techniques have been described that attempt to facilitate prosthesis positioning during a TKA procedure. Some techniques, such as those described in U.S. Pat. No. 5,733,292, involve trial prosthesis components which are used after femoral and tibial bone cuts are made to assess ligament tension. Other concepts such as the one disclosed in U.S. Pat. No. 8,491,589 incorporate aspects of ligament balancing and pressure sensing in the final prosthesis components. Some devices, such as those described in US 2003/0187452, are used to measure a gap between the distal femur and proximal tibia in extension and to help a surgeon recreate that same gap when the knee is in flexion. Other "gap checking" devices are described in U.S. Pat. No. 6,575,980. A method for approximating a preferred fit of a prosthesis is proposed in U.S. Pat. No. 8,078,440. A method and means for measuring ligament tension is disclosed in U.S. Pat. No. 4,964,862. Related, WO 201282628 discloses a system and method for presenting force information related to a provisional device. Furthermore, US 2015/0238204 discloses a surgical orientation system and method. A dynamic knee balancer with pressure sensing involving a prosthesis with a femoral portion and a tibial portion is described in U.S. Pat. No. 8,491,589. Other devices have been developed to help applying an amount of ligament tension or to apply a desired amount of tension to the ligaments. U.S. Pat. No. 4,501,266, for example, describes a knee distraction device for applying a desired amount of tension. Furthermore, EP 2 110 077 discloses a device and method for measuring joint-relating distances. Many paddle-like devices have been suggested for applying or measuring tension across a knee joint, such as the devices described in U.S. Pat. Nos. 5,597,379; 5,540,696; 5,800,438; 5,860,980; 5,911,723; 6,022,377; 8,211,041; and EP 2 559 386. U.S. Pat. No. 5,713,897 presents an anterior cruciate ligament tensioning device and method for its use. A problem with all these devices and techniques is their complexity in use, due to difficulty in attaching the proposed device to the patient's knee and/or leg, and/or due to a lack of modularity, because the proposed means for measuring is incorporated in the prosthesis components as an integral whole. Besides, concepts such as the method proposed in U.S. Pat. No. 8,078,440 are prone to errors because they rely on computer simulations without robust means of measuring.

U.S. Pat. No. 4,8,813,435 discloses a device adapted for replaceable implantation in soft body tissue for the measurement of the mechanical behavior of the soft tissues of the body. The device consists of a Hall-effect strain transducer that detects the linear motion of a magnetic core. A barb force transducer uses a barbed probe that is inserted into the soft tissue. The barb force transducer has pressure sensors located within the body of the probe that detect the squeezing of the tissue fibers against the sides of the transducer. The combination of the Hall-effect strain transducer and the barb force transducer allows the operator to simultaneously measure the strain and force on a specific soft tissue. A problem with the device according to, e.g., U.S. Pat. No. 4,8,813,435 is that only a single Hall sensor is provided. This makes the device prone to noise interference. Furthermore, the sliding magnetic core is essentially cylindrical and may therefore rotate within its slot. This leads to lack of robustness in the device's operation, as core rotation may lead to inaccuracy in the measuring, There remains a need in the art for an improved method for measuring strain in ligaments without requiring cutting of fibers of one or both collateral ligaments or requiring making cuts in the femur, tibia or fibula. Moreover, a solution is needed that reduces the complexity with respect to current approaches, simplifying attaching a measurement device to the patient, while being modular, by not incorporated parts of a measurement device in the prosthesis components. Furthermore, an improved device is needed which allows for robust and reliable measurement.

The present invention aims to resolve at least some of the problems mentioned above, avoiding cutting of ligaments for measurement purposes.

The invention thereto aims to provide a device for measuring ligament strain, as well as a system, a kit and a method relating to measuring ligament strain.

SUMMARY OF THE INVENTION

The present invention serves to increase functional performance (e.g., biomechanical function), increase durability (e.g., reduced wear), reduce or eliminate abnormal motion (e.g., paradoxical motion), and create a more natural post-operative feeling (e.g., improved proprioception) for said individual patient. By interpreting and understanding the pre-operative strain measurements of a patient's knee or other joint and comparing these to intra-operative strain values measured during operation, a surgeon may improve the overall result of the operation iteratively. Overall, the surgeon needs to take into account the six degrees of freedom characteristic of three-dimensional space motion: forward/backward, up/down, left/right, combined with changes in orientation through rotation about three axes. For instance, the surgeon may consider any or any combination of the following: optimizing implant sizing, medial/lateral positioning of a selected prosthesis, selecting one or more proper prosthetic components from any given number of standard or custom prosthesis designs from one or more orthopedic manufacturers. Furthermore, existing techniques often don't correlate with the patient body's own sensing mechanism, being the ligaments.

In a first aspect, the present invention concerns a device suitable for measuring the difference between a strain in a ligament at a first point in time and said strain at a second point in time, said device comprising
  a first ligament-retaining element adapted to be fastened on said ligament;
  a second ligament-retaining element adapted to be fastened on said ligament near said first ligament-retaining element;
  a wire fastened on said first ligament-retaining element;
  a bridging element comprising a distal end, a proximal end and a wire guiding channel for guiding said wire essentially between said distal end and said proximal end, the distal end of said bridging element fastened on said second ligament-retaining element;
  a sensor configured to measure a strain-indicating parameter representing a position of said wire relative to the proximal end of the bridging element for obtaining said difference between said strain in said ligament at said first point in time and said strain at said second point in time.

A key advantage of said device over devices known in the state of the art is that in their combination, said ligament-retaining elements, said bridging element and said wire allow to translate strains in said ligament into relative motion of a wire end near to said ligament, which are then transferred unchangingly to relative motion at the other, possibly remote end of the wire. This is a useful feature of said device, since it allows to measure strain of the ligament from a remote point rather than measuring strain immediately on the ligament. Measurement can thus take place outside of the sterile zone. Furthermore, said ligament-retaining elements can be miniaturized and may therefore interfere minimally with the ligament. Additionally, they may be produced cheaper with reduced size. Importantly, said device enables measurement without a continuously tensioned wire, since the wire can move freely through the bridging element.

In a further aspect, the present invention concerns a device as described above, whereby a portion of said wire is composed of a material with low deformation under tensile stress and/or compressive stress and/or bending, preferably metal, more preferably nitinol. This is useful because it allows to perform said transfer unchangingly, with the least deviation possible.

In a further aspect, the present invention concerns a device as described above, whereby said wire comprises a proximal wire portion near said proximal end of said wire guiding channel and a distal wire portion near said distal end of said wire guiding channel, whereby said distal wire section is composed of a material with low deformation under tensile stress and/or compressive stress and/or bending, preferably metal, more preferably nitinol, and whereby said proximal wire section comprises a proximal wire end and preferably a spacer wire section, whereby said proximal wire end is composed of a ferromagnetic material, preferably a ferromagnetic metal, whereby said spacer wire section is composed of a material with low electrical conductivity, preferably an electrically insulating material, more preferably electrically insulating plastic. This type of wire composition is preferable over a wire composition using a single material such as nitinol, because it facilitates the measurement by said sensor. More precisely, in an embodiment where the sensor uses an electromagnetic principle in its operation, for instance in a further preferred embodiment in which said sensor is a transducer comprising a linear variable differential transformer. In such case it is particularly useful to use a ferromagnetic metal or similar composition for the outer end of said wire, since it improves the electromagnetic response involved in the measurement. Measurement is further enhanced if said ferromagnetic metal is shielded from the rest of the wire by means of said spacer, avoiding interference of undesired electromagnetic signals in the measurement.

In a further aspect, the present invention concerns a device as described above, whereby said sensor is a transducer, preferably comprising a linear variable differential transformer, which converts a position of said wire into an unconditioned electrical signal carrying said strain-indicating parameter. Such a type of transducer is known to be adapted for accurate and compact functioning for said measuring.

In a further aspect, the present invention concerns a device as described above, whereby said sensor resides in a sensor unit, said sensor unit comprising a positioning means for accurate positioning of said sensor, whereby said positioning means is preferably adjustable to allow calibration, preferably comprising any or any combination of the following: a spring; a screw; an inner housing enveloping the sensor and enveloped by an outer housing, whereby said positioning defines the relative position of said inner housing with respect to said outer housing. This type of housing is useful because it allows robust operation of said device, as well as accurate calibration of said device.

In a further aspect, the present invention concerns a device as described above, whereby said first ligament-retaining element and said second ligament-retaining element are adapted to be fastened on said ligament by sewing, preferably through the use of sewing thread, preferably biocompatible sewing thread. Said type of fastening provides a secure mode of fastening, while causing minimal damage to said ligament.

In a further aspect, the present invention concerns a device as described above, whereby said bridging element comprises a coil wound around said wire, whereby said wire comprises a permanent magnet rod near said coil, whereby an electric current flowing through said coil exerts a force on said magnet rod along a direction essentially parallel to said wire. This is useful because it provides an actuator function, allowing to measure not only ligament strain but also ligament slackness.

In a further aspect, the present invention concerns a system comprising a device as described above, whereby said system is suitable for evaluating the positioning of a knee prosthesis of a patient, said system comprising
  a device as described above;
  a signal conditioning unit, preferably comprising a conditioning module and a data acquisition module;
  a computer device comprising a processor; tangible, non-transitory memory; program code on said memory instructing said processor; preferably a display;
wherein said signal conditioning unit is configured to receive an unconditioned signal comprising said strain-indicating parameter from said sensor, said unconditioned signal preferably being an electrical signal with analog signal representation, and
wherein said signal conditioning unit is configured to transmit a conditioned signal, preferably an electrical signal with digital signal representation;
wherein said conditioning module is configured to condition said unconditioned signal originating from said sensor, and wherein said conditioning module is configured to transmit a conditioning module output signal, preferably an electrical signal with analog signal representation;
wherein said data acquisition module comprises a computer bus adapted to interface with said computer device, wherein said data acquisition module is configured to receive said conditioning module output signal, and wherein said data acquisition module is configured to transmit said conditioned signal, preferably an electrical signal with digital signal representation;
wherein said computer device is configured to receive said conditioned signal comprising said strain-indicating parameter from said computer bus of said data acquisition module, wherein said computer is configured to process said conditioned signal according to a plurality of processing purposes, including any or any combination of the following: calculation of a statistical quantity relating to said strain-indicating parameter, visualization of a diagram relating to said strain-indicating parameter, configuration of a system parameter relating to said sensor unit and/or said signal conditioning unit;
wherein said positioning comprises measuring the difference between a strain in a ligament at a first point in time and said strain at a second point in time, whereby said first point in time precedes the application of said knee prosthesis of said patient, and whereby said second point in time occurs simultaneously with said application of said knee prosthesis, whereby said evaluating of the positioning is positive if said difference is smaller than a given small value set beforehand, and negative in the opposite case.

Said system has key advantages since it allows for reliable operation by means of a standard computer device, with great ease of use for the person operating said system. Additionally, the system incorporates reliable modules that guarantee robust operation.

In a further aspect, the present invention concerns a system as described above, whereby said system comprises a multipurpose sensing module, and wherein said computer device comprises a computer network interface;
wherein said multipurpose sensing module comprises a sensing network interface and any or any combination of the following: an accelerometer, preferably a 3-axis accelerometer; a gyroscope; a magnetometer; a positioning meter;
wherein said multipurpose sensing module is configured for measuring a sensing parameter regarding a position relating to said patient; and whereby said multipurpose sensing module is configured to transmit said measurement of said sensing parameter to said computer device via said sensing network interface, preferably according to a wireless protocol, more preferably Wi-Fi or ZigBee or Wireless USB, most preferably Bluetooth;
wherein said computer device is configured to receive said measurement of said sensing parameter from said multipurpose sensing module via said sensing network interface, preferably according to a wireless protocol, more preferably Wi-Fi or ZigBee or Wireless USB, most preferably Bluetooth; and whereby said computer device is configured to derive a flexion of said knee of said patient from said sensing parameter, and whereby said computer device is configured to process said sensing parameter and/or said flexion according to a plurality of processing purposes, including any or any combination of the following: calculation of a statistical quantity relating to said sensing parameter and/or said flexion, visualization of a diagram relating to said sensing parameter and/or said flexion, configuration of a system parameter relating to said multipurpose sensing module;

wherein said evaluating of the positioning takes into account said sensing parameter and/or said flexion in relation to said strain-indicating parameter, optionally whereby said evaluating of the positioning is positive if said difference for a measured flexion is smaller than a given small value that is function of said measured flexion according to a function set beforehand, and negative in the opposite case.

Such a system has the advantage that more information is available to the operation said system, e.g. by being provided with information regarding the flexion of the joint to which said ligament belongs. Moreover, said multipurpose sensing devices, preferably implemented wirelessly, can be attached in the proximity of said ligament without contact with the ligament, creating no risk of damaging said ligament.

In a further aspect, the present invention concerns the use of a sensor as described above, said use comprising the steps of
  (A) fixating a first and a second ligament-retaining element on a ligament, preferably by sewing;
  (B) removing an installing housing and/or a fixating pin if said installing housing and/or said fixating pin is present;
  (C) attaching a wire to said sensor by attaching a wire-relating mechanical connector to a sensor-relating mechanical connector;
  (D) calibrating said sensor by means of a calibration means if said calibration means is present;
  (E) measuring a difference between a strain in said ligament at a first point in time and said strain at a second point in time.

In a further aspect, the present invention concerns a computer program product for use in a computer device belonging to a system as described above, said computer program product including a plurality of computer executable instructions stored on a computer readable medium, wherein said computer comprises a display, wherein said instructions, when executed by said computer device, cause the computer device to perform the steps of:
  (I) receiving a conditioned signal comprising a strain-indicating parameter from a computer bus of a data acquisition module,
  (II) processing said conditioned signal according to a plurality of processing purposes, including any or any combination of the following: calculation of a statistical quantity relating to said strain-indicating parameter, visualization of a diagram relating to said strain-indicating parameter, configuration of a system parameter relating to said sensor unit and/or said signal conditioning unit;
  (III) optionally, receiving a measurement of a sensing parameter from a multipurpose sensing module via a sensing network interface, preferably according to a wireless protocol, more preferably Wi-Fi or ZigBee or Wireless USB, most preferably Bluetooth;
  (IV) optionally, deriving a flexion of a knee of a patient from said sensing parameter,
  (V) optionally, process said sensing parameter and/or said flexion according to a plurality of processing purposes, including any or any combination of the following: calculation of a statistical quantity relating to said sensing parameter and/or said flexion, visualization of a diagram relating to said sensing parameter and/or said flexion, configuration of a system parameter relating to said multipurpose sensing module;
  (VI) showing said processed conditioned signal and optionally said processed sensing parameter on said display;

In a further aspect, the present invention concerns a kit comprising kit elements for mounting a device as described above, said kit comprising
  a sensor, comprising a sensor-relating mechanical connector;
  at least one patient-specific wire kit, said patient-specific wire kit comprising a first ligament-retaining element; a second ligament-retaining element; a wire; said bridging element; a wire-relating mechanical connector; optionally, an installing housing; optionally, a fixating pin;
  whereby said wire comprises a proximal wire portion near said proximal end of said wire guiding channel and whereby said proximal wire portion is optionally enveloped by said installing housing, optionally held in place by said fixating pin;
  whereby said sensor-relating mechanical connector and said wire-relating mechanical connector are adapted for mutual and reversible attachment, preferably screwing or clipping.

Such a kit has the advantage of providing a hygienic and patient-friendly approach. More precisely, by reusing said sensor but disposing said patient-specific wire kit after use, one may use said device in a hygienic and responsible way while not wasting resources by reusing said sensor.

In a further aspect, the present invention concerns a method for using a kit as described above and in the claims, said method comprising the steps of
  (a) fixating a first and a second ligament-retaining element on a ligament, preferably by sewing;
  (b) removing an installing housing and/or said fixating pin if said installing housing and/or said fixating pin is present;
  (c) attaching a wire to a sensor by attaching a wire-relating mechanical connector to a sensor-relating mechanical connector;
  (d) calibrating said sensor by means of a calibration means if said calibration means is present;
  (e) measuring said difference between said strain in said ligament at a first point in time and said strain at a second point in time.

This method has the advantage of requiring minimal time between the moment of sewing said ligament-retaining elements to said ligament and the end of the measurements. This advantage is important since it further helps reducing the risk of harming said ligament during the method.

In a further aspect, the present invention concerns a method, for evaluating the positioning of a knee prosthesis of a patient, said method comprising the steps of
  (i) fastening a wire on a first ligament-retaining element, preferably by gluing;
  (ii) guiding said wire through a wire guiding channel of a bridging element, said bridging element comprising a distal end, a proximal end and said wire guiding channel for guiding said wire essentially between said distal end and said proximal end,
  (iii) fastening said distal end of said bridging element on a second ligament-retaining element, preferably by gluing;

(iv) fixating said first and said second ligament-retaining element on a ligament of said patient, preferably by sewing;
(v) attaching said wire to a sensor by attaching a wire-relating mechanical connector to a sensor-relating mechanical connector attached to said sensor, whereby said sensor is configured to measure a strain-indicating parameter representing a position of said wire relative to the proximal end of the bridging element for obtaining a difference between a strain in said ligament at a first point in time and a strain at a second point in time;
(vi) calibrating said sensor by means of a calibration means if said calibration means is present;
(vii) measuring a native strain in said ligament by means of said sensor, a signal conditioning unit, a computer device, and optionally measuring a flexion and/or a sensing parameter associated with said native strain by means of an optional multipurpose sensing unit;
(viii) positioning said knee prosthesis;
(ix) evaluating the positioning of said knee prosthesis at a current point in time by measuring the difference between said native strain in said ligament and a strain at said current point in time; optionally taking into account a flexion and/or a sensing parameter associated with said current point in time;
whereby said evaluating of the positioning is positive if said difference is smaller than a given small value set beforehand causing the method to end, and negative in the opposite case causing a return to step (viii).

This method is advantageous when compared to existing methods because it allows for fast measurement as well as fast positioning of said knee prosthesis. A key advantage is that by reducing the time required for positioning helps reducing the risk of harming said ligament during the method. Another key advantage is that by using said method, both the positioning and the evaluation of said positioning can be done repeatedly and as a result more accurately. This is mainly due to the fact that a single action of positioning and evaluating takes up only a very short time. This is not realistic with existing methods, because said positioning and evaluating takes up too much time and/or lacks accuracy.

According to another aspect of the current invention, the invention relates to an integrated device suitable for measuring the difference between a strain in a ligament at a first point in time and said strain at a second point in time, said integrated device comprising
a ligament-attaching element adapted to be fastened on said ligament;
a slider module adapted to be fastened on said ligament near said first ligament-attaching element, said slider module comprising a slider guiding channel;
a slider comprising a distal slider end and a proximal slider end, said distal slider end fastened on said ligament-attaching element, said proximal slider end guided in said slider guiding channel;
a sensor configured to measure a strain-indicating parameter representing a position of said proximal slider end for obtaining said difference between said strain in said ligament at said first point in time and said strain at said second point in time, wherein said sensor comprises a Hall sensor, preferably a linear Hall sensor, which converts a position of said proximal slider end into a conditioned electrical signal carrying said measurement of said strain-indicating parameter.

A key advantage of said integrated device lies in the compactness of the device, since only a limited number of components is involved, which may be implemented very compactly. Another advantage is the high precision of the measurements enabled by said Hall sensor, allowing measurements with micrometer precision. Another advantage is the reduced electromagnetic interference when compared to the state of the art, due to the use of a Hall sensor. The latter is important especially in a hospital environment where a multitude of electrical equipment is present.

In a preferred embodiment of the integrated device according to the present invention, said sensor comprises two or more Hall sensors for robust measurement, said Hall sensors placed in close proximity. This has the advantage of yielding an increased measurement range and/or increased precision for the device, as well as improved robustness. Specifically, the use of more than one Hall sensor allows to remove the drawbacks known from related devices in the prior art, such as the device disclosed in U.S. Pat. No. 4,813,435. According to U.S. Pat. No. 5,777,467 (col. 1, l. 24-26), the device disclosed in U.S. Pat. No. 4,813,435 exhibits difficulties such as noise interference, core rotation artifact and limited linear range. At least one of these difficulties, and preferably all of these difficulties, are overcome by using more than one Hall sensor as described by the present invention.

In a preferred embodiment of the integrated device according to the present invention, the slider module comprises a slider module length, a slider module width and a slider module height; whereby either of said slider module length and said slider module width is not larger than 18 mm, more preferably not larger than 15 mm, and most preferably not larger than 12 mm; whereby said slider module height is not larger than 8 mm, preferably not larger than 6 mm, most preferably not larger than 4 mm; and whereby said slider is not longer than 30 mm, preferably not longer than 20 mm, more preferably not longer than 18 mm. In an alternative embodiment, either of said slider module length and said slider module width is larger than 18 mm but not larger than 40 mm. In a further alternative embodiment, said slider module height is larger than 8 mm but not larger than 20 mm. In a further alternative embodiment, said slider is longer than 30 mm but not longer than 60 mm.

This high degree of compactness is beneficial since it allows easy attachment of the device to the patient. Moreover, the compactness leads to a lighter weight for the device, reducing the risk that the ligament is damaged in any way by the device with which it is in contact.

In a preferred embodiment of the integrated device according to the present invention, said integrated device further comprises a transmitter module, preferably a low-power transmitter module, said transmitter module configured to transmit said measurement of said strain-indicating parameter to a computer device, preferably according to a wireless protocol, more preferably Wi-Fi or ZigBee or Wireless USB, most preferably Bluetooth, and whereby said integrated device comprises a power source, preferably a battery, whereby said integrated device is adapted to operate entirely within a sterile zone in close proximity to said ligament, without any cable going beyond said sterile zone. This is particularly useful since it allows implementation of the entire device as a sterile, stand-alone patch. This sterile patch, preferably a single-use sterile patch, can be attached entirely within the confines of the small sterile zone surrounding the ligament. This is advantageous since it reduces the risk of surgery complications relating to infections. Furthermore, it enhances security in the operation room, eliminating the risk of, e.g., patient injury due to accidental pulling of a cable.

According to another aspect of the current invention, the invention relates to an integrated system suitable for positioning of a knee prosthesis of a patient, said system comprising

- the integrated device according to the present invention;
- a computer device comprising a processor; tangible, non-transitory memory; program code on said memory instructing said processor; preferably a display;

wherein said computer device is configured to receive said measurement of said strain-indicating parameter and/or said measurement of said sensing parameter, wherein said computer is configured to process said measurement of said strain-indicating parameter and/or said measurement of said sensing parameter preferably according to a plurality of processing purposes, including any or any combination of the following: calculation of a statistical quantity relating to said strain-indicating parameter and/or said sensing parameter, visualization of a diagram relating to said strain-indicating parameter and/or said sensing parameter, configuration of a system parameter relating to said sensor and/or said integrated sensing module, derivation of a flexion of said knee of said patient from said measurement of said sensing parameter;

wherein said computer device is configured for computing a difference between a strain in a ligament at a first point in time and said strain at a second point in time, whereby said first point in time precedes the application of said knee prosthesis of said patient, and whereby said second point in time occurs simultaneously with said application of said knee prosthesis, said difference thereby being indicative of the positioning of said knee prosthesis.

According to another aspect of the current invention, the invention relates to an computer program product for use in a computer device belonging to an integrated system according to the present invention, said computer program product including a plurality of computer executable instructions stored on a computer readable medium, wherein said computer preferably comprises a display, wherein said instructions, when executed by said computer device, cause the computer device to perform the steps of:

(01) receiving a first measurement of said strain-indicating parameter and/or a measurement of said sensing parameter from said integrated device;

(02) receiving a second measurement of said strain-indicating parameter and/or a measurement of said sensing parameter from said integrated device,

(03) computing a difference between said first and said second measurement of said strain-indicating parameter and/or said measurement of said sensing parameter preferably according to a plurality of processing purposes, including any or any combination of the following: calculation of a statistical quantity relating to said strain-indicating parameter and/or said sensing parameter, visualization of a diagram relating to said strain-indicating parameter and/or said sensing parameter, configuration of a system parameter relating to said sensor and/or said integrated sensing module, derivation of a flexion of a knee of a patient from said measurement of said sensing parameter,

(04) communicating a result of step (03) relating to said strain-indicating parameter and/or said sensing parameter, preferably by showing said result on said display.

Hereby, the computer program product can be used in a computer device, such as the computer device used in a system according to the present invention.

According to another aspect of the current invention, the invention relates to a kit comprising said integrated device and a knee prosthesis adapted for total knee arthroplasty. This is helpful for medical personnel since it ensures that the knee prosthesis used belongs to the category of knee prosthesis devices that are suitable to be positioned aided by said integrated device.

Further embodiments are discussed in the detailed description and the dependent claims.

DETAILED DESCRIPTION OF THE INVENTION

Figure 1:
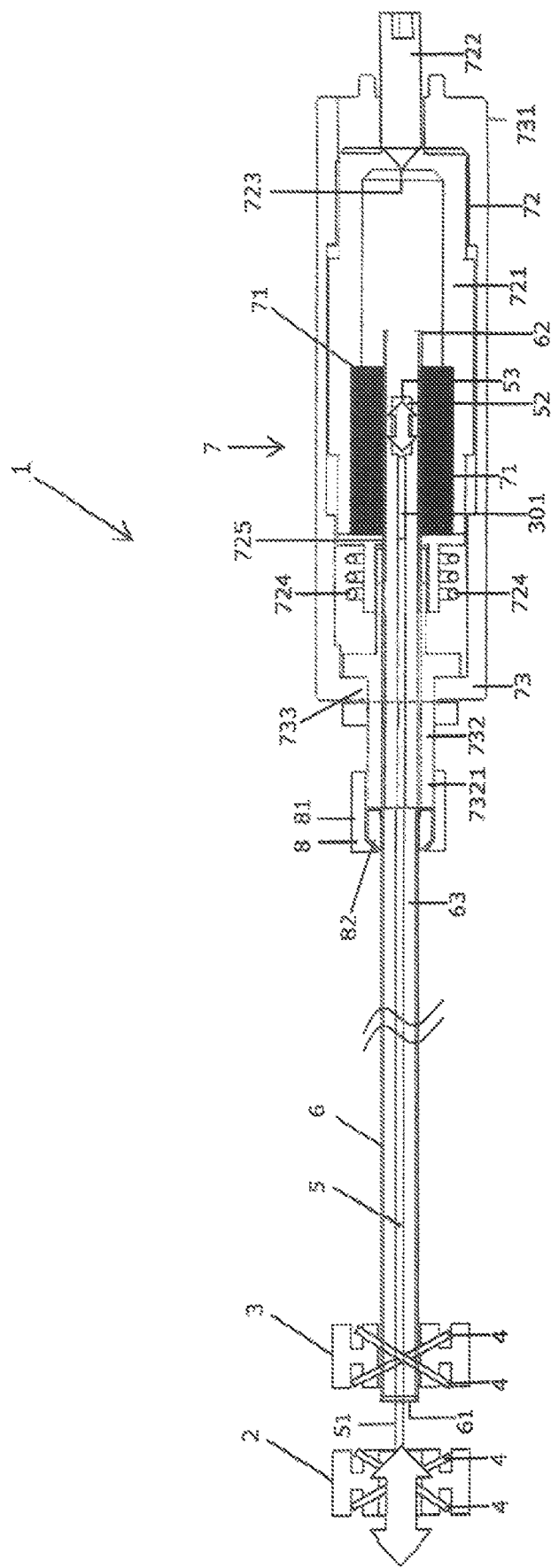
FIG. 1 shows a first embodiment according to the present invention.

The present invention concerns a device for measuring ligament strain, as well as a system, a kit and a method relating to measuring ligament strain.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

The acronyms "MCL", "TCL" and "LCL" stand for "medial collateral ligament", "tibial collateral ligament" and "lateral collateral ligament", respectively. These terms belong to anatomical terminology, referring to major ligaments of the knee. In the context of this document, the terms "MCL" and "TCL" are interchangeable. Furthermore, the term "collateral ligament" refers to either one of said ligaments, i.e. the medial collateral ligament or the lateral collateral ligament.

In the context of this document, the following terms are interchangeable: "ligament-retaining element" and "fixating block", "prosthesis" and "implant".

In an embodiment of the invention, the bridging element has a tubular shape and envelops the wire guiding channel. In such case, said wire guiding channel is the central cavity of said bridging element, and is referred to as "lumen".

In this document, ligament strain and ligament slackness are two distinct parameters describing different aspects of the condition of a ligament. The ligament strain refers to the tightness with which the ligament is stretched. The ligament slackness, on the other hand, refers to the looseness of the ligament, whereby a high degree of slackness may be indicative of bulging and/or buckling of the ligament.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The device disclosed in this invention is suitable for strain and/or slackness measurement in soft tissue (i.e. ligament, capsule, tendon, muscle or other soft tissue structure), but also tension between bones or parts of bones, tension between bones or part of bones and implants, furthermore tension between orthopedic implants/devices or parts of implants/devices. These tissues (soft tissue and bones), implants and devices are located in all parts of the locomotor system, i.e. all joints, tendons, capsule, muscles and bones of the human body. In a further preferred embodiment of the present invention, said ligament is a ligament relating to the human knee. In a further preferred embodiment, said ligament is a collateral ligament. In an alternative embodiment, said ligament does not relate to the human knee but to another joint, or it connects two bones or cartilages. In another alternative embodiment, said ligament connects two pieces of bone, e.g. in case of a fracture with osteosynthesis. In the latter case, measurement of strain can be performed to evaluate the relative positioning of two pieces of bone during and after surgery. In a further alternative embodiment, said ligament connects a bone and an implant, e.g. for evaluating the positioning of a prosthesis in Total Hip Arthroplasty (THA). In a further alternative embodiment, said ligament connects two devices, e.g. for evaluating the positioning of said first and second device in surgery with Patella in Place Balancer (PIPB). In a further alternative embodiment, said ligament connects a bone and/or an implant with soft tissue, e.g. for evaluating the strain between a bone and/or implant and any of the following: a tendon, a fascia, a capsule.

The sensor is adapted for placement on the soft tissue, bone, implant or other device of a (living or dead) human or animal and produces an output which is a measurement of the tensile force/displacement/length change applied to this soft tissue or bony structure, also in applications between soft tissue and bone, bone to bone, bone to implant, bone to device as to situations were strain/displacement/length change is measured between parts of an implant or device used in the locomotor system.

In some applications the sensor data is related to a joint angle/relative 3D position/orientation multipurpose sensor module responsive to the range of motion of the body.

It is anticipated that by utilizing the method steps provided by the present invention, final positioning of a knee prosthesis within the patient's joint is optimized to reduce quadriceps misfire and strain, reduce implant loosening and subluxation, maintain balanced soft-tissue envelopes, reduce implant wear (by positioning implant components in such a way that magnitudes and directions of frictional forces experienced during a patient's typical biomechanical functions are minimized), reduce or eliminate abnormal motion, and give the patient a more natural postoperative feeling.

Modifying ligament tension during TKA surgery is complicated by the fact that the natural knee does not operate like a hinge moving about a single axis. The knee exhibits dynamic external rotation of the tibia relative to the femur as the knee moves from its flexed to its fully extended position. This automatic rotation of the tibia occurs in the opposite direction when the knee is flexed from its fully extended position to produce an internal rotation of the tibia relative to the femur. Thus, the natural knee exhibits a rotary laxity that allows the tibia to rotate through a limited internal and external arc, during knee flexion. Additionally, the femur translates anteriorly and posteriorly as the tibia is being flexed about it, bringing yet another movement variable into the equation. Thus, the ligaments of the knee, along with the femur, tibia and patella, create a truly dynamic bio-mechanism, making ligament tension balancing in TKA surgery extremely challenging. In this context, controversy exists whether restoration of neutral mechanical alignment should be attempted in all patients undergoing TKA. In fact, restoration of constitutional rather than neutral mechanical alignment may in theory lead to a more physiological strain pattern in the collateral ligaments; therefore, it could potentially be beneficial to patients.

In a preferred embodiment of the invention, said bridging element is tubular-shaped, in the form of a tube shaft. In a further preferred embodiment, said tube shaft is braid and coil reinforced. Possible materials for said tube shaft are PTFE and polyimide. Primary advantages of using PTFE and polyimide for the tube shaft include increased column strength, torque transmission and increased burst strength. In a further preferred embodiment, the tube shaft consists of a substrate layer, a braided or coiled layer, and an exterior layer. Possible substrates are any or any combination of the following: polyimide, PTFE composite, pure PTFE liner. Hereby, a pure PTFE liner and a PTFE composite may offer reduced surface friction. Possible materials for the exterior layer are any or any combination of the following: polyimide, pebax, nylon, or a urethane.

In a preferred embodiment of the invention, strain is measured using a sensor unit. The sensor unit converts a mechanical displacement input signal into an unconditioned electrical signal. The sensor unit comprises a sensor. In one embodiment, said sensor comprises a linear variable differential transformer (LVDT). In another embodiment, said sensor comprises a half-bridge. The LVDT and half-bridge are two alternative transducer embodiments to convert said mechanical displacement signal into an unconditioned electrical signal. According to a preferred embodiment, said LVDT is implemented as an electrical transformer comprising a primary LVDT coil and a secondary LVDT coil. According to another preferred embodiment, said half-bridge is implemented as an electrical convertor comprising a half-bridge coil.

In a preferred embodiment of the invention, said strain-indicating parameter is transmitted by said sensor by means of an electrical signal referred to as unconditioned electrical signal in the following. Said unconditioned electrical signal is fed to a signal conditioner unit by means of a signal cable. Said signal conditioner unit converts said unconditioned electrical signal into a conditioned electrical signal. Hereby, said signal cable carries said unconditioned electrical signal to said strain sensor signal conditioner. In a preferred embodiment, said cable is standard equipment wire such as 7/0.2 (24AWG) which can be twisted together, or a generic CAT5 UTP cable. In a more preferred embodiment, said cable is adapted for use in industrial and/or medical environments where there is a plurality equipment likely to produce significant levels of electrical interference requiring the use of a screened cable, e.g. braided or foil screened cable. In a further preferred embodiment, said signal conditioner unit comprises a conditioning module (CM). In a further preferred embodiment, said signal conditioner unit may comprise a data acquisition module (DAQ) and/or an analog connector interface. Hereby, said CM receives said unconditioned electrical signal carrying said strain-indicating parameter, preferably using an analog signal representation, conditioning said signal originating from the sensor. Hereby, said conditioning comprises gain control and offset control of said electrical signal. The output of said CM, in a preferred embodiment still in an analog signal representation, is fed to any or a combination of the following: said DAQ, said analog connector interface. Said DAQ converts said output of said DAQ to a conditioned signal, preferably using a digital signal representation. Said DAQ hereby functions as a device that digitizes incoming analog signals so that a computer can interpret them. In a preferred embodiment, said DAQ comprises any or any combination of the following: signal conditioning circuitry for additional signal conditioning, an analog-to-digital converter (ADC), and a computer bus for interfacing with a computer device. Additionally, said DAQ may comprise any or any combination of the following: a digital-to-analog converter (DAC) to output analog signals, a digital I/O line to input and/or output a digital signal, and a counter/timer to count and/or transmit digital pulses. In a preferred embodiment, said conditioned signal is fed to a computer device. In a preferred embodiment, said output of said CM is alternatively/additionally fed to a connector interface, preferably a pair of current output connectors, more preferably a pair of voltage output connectors. In a preferred embodiment, said CM and/or said DAQ and/or said signal conditioner unit as a whole comprises a metal case which provides for electromagnetic shielding. In a further preferred embodiment, said case is connected to a local ground, e.g. via an EMC cable gland and/or a mounting bracket. In further preferred embodiments of the invention, said CM and/or said DAQ is adapted for any or any combination of the following: wide gain range allowing a wide range of transducers to be connected without the need for attenuation resistors, fixed and variable offsets facilitating setting of uni-polar output, full independency of gain and offset adjustment, selectable transducer excitation frequency, selectable transducer load resistances, selection between forward and reverse connection, full CE compliance.

In an alternative embodiment, said sensor comprises the entire signal conditioner unit, leading to a more compact implementation in terms of physical footprint.

In a further preferred embodiment, said conditioned signal is fed to a computer device. Said computer device may be any of the following: a smartphone, a tablet, a watch, a laptop computer, a desktop computer, a microcontroller-based computing device. In a preferred embodiment, said computer device comprises program code and a display. Hereby, said display serves for visual representation of the received data, and said program code corresponds to a computer program product, adapted to receive a strain-indicating parameter from the sensor measuring said parameter, processing received data according to the needs of an end user of the computer program product. Said needs may include any or any combination of the following: calculation of statistical quantities derived from the received data, modes of visualization of the data, configuration parameters to be fed back to the sensor unit and/or the signal conditioning unit.

In a further preferred embodiment, said computer device additionally receives a sensing parameter relating to a position of said patient from a multipurpose sensing module (MSM), whereby said computer device additionally comprises an interface to receive data from said MSM, and said computer program product is adapted to process and display said sensing parameter. In a preferred embodiment, said sensing parameter is received over a wireless channel by means of a wireless technology, preferably associated with a wireless technology standard, e.g. Wi-Fi or ZigBee or Wireless USB, more preferably Bluetooth. In an alternative embodiment, said sensing parameter is received by said computer from said MSM via a physical cable. In a more preferred embodiment, a pair of said MSMs is present on the body of a patient near to said ligament and on opposite sides of said ligament for which the strain is measured. In a preferred embodiment, said MSM comprises any or any combination of the following: an accelerometer, preferably a 3-axis accelerometer; a gyroscope; a magnetometer. In a further preferred embodiment, said MSM comprises a positioning meter. In a preferred embodiment, a purpose of said pair of MSMs is to track the movement of a limb of said patient during movement of the joint to which said ligament belongs. Particularly, the use of the 3-axis data measurements by means of said 3-axis accelerometer belonging to said pair of MSMs (if present) allows for accurate positioning of said MSMs, in its turn allowing to derive information regarding the position of said limb of said patient, and, more importantly, of the current angle of said joint of said patient. In its turn, this allows accurate determination of the conditions in which a strain measurement is made. In a further preferred embodiment, a further purpose of an MSM is to measure changes in the electromagnetic environment in which the strain measurement takes place. Particularly, the use of said magnetometer belong to said MSM (if present) allows accurate measurement of said electromagnetic environment. This is important particularly if the embodiment involves an electromagnetic principle in the operation of the sensor, as is the case for a sensor comprising a linear variable differential transformer. In such case, electromagnetic interference with the environment may negatively impact the quality of the measurements. Such interference may originate from the plurality of equipment typically present in a medical environment, but may also be caused e.g. by the presence of a simple piece or plate of metal in the immediate surrounding of the measurement.

In an alternative embodiment, said MSM does not transmit sensing parameter to said computer device but instead to any or a combination of the sensor unit and the signal conditioning unit. In a further alternative embodiment, said MSM is not a separate module but rather comprised in any or a combination of the sensor unit and the signal conditioning unit, which allows for a more compact implementation in terms of physical footprint.

In one embodiment of the present invention, said ligament-retaining element is composed of metal and is sewed on the ligament. In an alternative embodiment, said ligament-retaining element may be attached to said ligament purely by means of microneedles, without requiring any other mode of attachment such as sewing. Particularly, adhesion of said fixating block may be realized by using a biphasic microneedle array attached to the back of said fixating block, allowing penetration in and attachment to said ligament with minimal insertion force and depth, yet high adhesion strength. Hereby, the biphasic microneedle array mechanically interlocks with tissue through swellable microneedle tips. A specific implementation of said biphasic microneedle array is described in Yang, S Y et al., "A bio-inspired swellable microneedle adhesive for mechanical interlocking with tissue," Nature Communications, Vol. 4:1702, 2013, 1-10.

In a further preferred embodiment of the present invention, the evaluation of the positioning of a knee prosthesis of a patient comprises the use of said device suitable for measuring the difference between a strain in a ligament at a first point in time and said strain at a second point in time, as well as two multipurpose sensing modules. Hereby, said two multipurpose sensing modules preferably comprise an accelerometer. In order to perform said evaluation of the positioning, the ligament-retaining elements are attached to a ligament of the patient's knee, preferably a collateral ligament. Furthermore, a first sensing module of said two sensing modules is attached to the patient's tibia, preferably near the ankle, and a second sensing module of said two sensing modules is attached to the patient's femur, preferably near the hip. After calibration, measurement can be performed. Said measurement comprises measurement of the ligament tension and/or the ligament slackness, by means of said device. Said measurement further comprises measurement of the flexion during movement of the knee. In a preferred embodiment, the accelerometer measurements of both sensing modules are tracked over time during movement of the knee, obtaining a flexion measurement over time. In a further preferred embodiment, said flexion measurement over time is done while the knee is flexed vertically, i.e. the two sensing modules remain in a common vertical plane. The latter allows to derive very accurate direct measurements of the flexion from the accelerometer measurements. In an alternative embodiment, said flexion measurement over time is done according some three-dimensional profile, and a plurality of three-dimensional movement measurements, possibly comprising the flexion, is derived from said accelerometer measurements. By combining the measurements of ligament strain and/or ligament slackness over time with the measurements of flexion and/or other three-dimensional movement, a more accurate evaluation of the positioning of said knee prosthesis can be realized, leading to a superior positioning.

The invention therefore relates, but is not limited in any way by the following points:

1. A device suitable for measuring the difference between a strain in a ligament at a first point in time and said strain at a second point in time, said device comprising
   - a first ligament-retaining element adapted to be fastened on said ligament;
   - a second ligament-retaining element adapted to be fastened on said ligament near said first ligament-retaining element;
   - a wire fastened on said first ligament-retaining element;
   - a bridging element comprising a distal end, a proximal end and a wire guiding channel for guiding said wire essentially between said distal end and said proximal end, the distal end of said bridging element fastened on said second ligament-retaining element;
   - a sensor configured to measure a strain-indicating parameter representing a position of said wire relative to the proximal end of the bridging element for obtaining said difference between said strain in said ligament at said first point in time and said strain at said second point in time.

2. A device according to the previous point, whereby a portion of said wire is composed of a material with low deformation under tensile stress and/or compressive stress and/or bending, preferably metal, more preferably nitinol.

3. A device according to point 1, whereby said wire comprises a proximal wire portion near said proximal end of said wire guiding channel and a distal wire portion near said distal end of said wire guiding channel, whereby said distal wire section is composed of a material with low deformation under tensile stress and/or compressive stress and/or bending, preferably metal, more preferably nitinol, and whereby said proximal wire section comprises a proximal wire end and preferably a spacer wire section, whereby said proximal wire end is composed of a ferromagnetic material, preferably a ferromagnetic metal, whereby said spacer wire section is composed of a material with low electrical conductivity, preferably an electrically insulating material, more preferably electrically insulating plastic.

4. A device according to any of the above points, whereby said sensor is a transducer, preferably comprising a linear variable differential transformer, which converts a position of said wire into an unconditioned electrical signal carrying said strain-indicating parameter.

5. A device according to any of the above points, whereby said sensor resides in a sensor unit, said sensor unit comprising a positioning means for accurate positioning of said sensor, whereby said positioning means is preferably adjustable to allow calibration, preferably comprising any or any combination of the following: a spring; a screw; an inner housing enveloping the sensor and enveloped by an outer housing, whereby said positioning defines the relative position of said inner housing with respect to said outer housing.

6. A device according to any of the above points, whereby said first ligament-retaining element and said second ligament-retaining element are adapted to be fastened on said ligament by sewing, preferably through the use of sewing thread, preferably biocompatible sewing thread.

7. A device according to any of the above points, whereby said bridging element comprises a coil wound around said wire, whereby said wire comprises a permanent magnet rod near said coil, whereby an electric current flowing through said coil exerts a force on said magnet rod along a direction essentially parallel to said wire.

8. A system suitable for evaluating the positioning of a knee prosthesis of a patient, said system comprising
   - a device according to any of the above claims;
   - a signal conditioning unit, preferably comprising a conditioning module and a data acquisition module;

a computer device comprising a processor; tangible, non-transitory memory; program code on said memory instructing said processor; preferably a display;

wherein said signal conditioning unit is configured to receive an unconditioned signal comprising said strain-indicating parameter from said sensor, said unconditioned signal preferably being an electrical signal with analog signal representation, and wherein said signal conditioning unit is configured to transmit a conditioned signal, preferably an electrical signal with digital signal representation;

wherein said conditioning module is configured to condition said unconditioned signal originating from said sensor, and wherein said conditioning module is configured to transmit a conditioning module output signal, preferably an electrical signal with analog signal representation;

wherein said data acquisition module comprises a computer bus adapted to interface with said computer device, wherein said data acquisition module is configured to receive said conditioning module output signal, and wherein said data acquisition module is configured to transmit said conditioned signal, preferably an electrical signal with digital signal representation;

wherein said computer device is configured to receive said conditioned signal comprising said strain-indicating parameter from said computer bus of said data acquisition module, wherein said computer is configured to process said conditioned signal according to a plurality of processing purposes, including any or any combination of the following: calculation of a statistical quantity relating to said strain-indicating parameter, visualization of a diagram relating to said strain-indicating parameter, configuration of a system parameter relating to said sensor unit and/or said signal conditioning unit;

wherein said positioning comprises measuring the difference between a strain in a ligament at a first point in time and said strain at a second point in time, whereby said first point in time precedes the application of said knee prosthesis of said patient, and whereby said second point in time occurs simultaneously with said application of said knee prosthesis, whereby said evaluating of the positioning is positive if said difference is smaller than a given small value set beforehand, and negative in the opposite case.

9. A system according to previous point 8, wherein said system comprises a multipurpose sensing module, and wherein said computer device comprises a computer network interface;

wherein said multipurpose sensing module comprises a sensing network interface and any or any combination of the following: an accelerometer, preferably a 3-axis accelerometer; a gyroscope; a magnetometer; a positioning meter;

wherein said multipurpose sensing module is configured for measuring a sensing parameter regarding a position relating to said patient; and whereby said multipurpose sensing module is configured to transmit said measurement of said sensing parameter to said computer device via said sensing network interface, preferably according to a wireless protocol, more preferably Wi-Fi or ZigBee or Wireless USB, most preferably Bluetooth;

wherein said computer device is configured to receive said measurement of said sensing parameter from said multipurpose sensing module via said sensing network interface, preferably according to a wireless protocol, more preferably Wi-Fi or ZigBee or Wireless USB, most preferably Bluetooth; and whereby said computer device is configured to derive a flexion of said knee of said patient from said sensing parameter, and whereby said computer device is configured to process said sensing parameter and/or said flexion according to a plurality of processing purposes, including any or any combination of the following: calculation of a statistical quantity relating to said sensing parameter and/or said flexion, visualization of a diagram relating to said sensing parameter and/or said flexion, configuration of a system parameter relating to said multipurpose sensing module;

wherein said evaluating of the positioning takes into account said sensing parameter and/or said flexion in relation to said strain-indicating parameter, optionally whereby said evaluating of the positioning is positive if said difference for a measured flexion is smaller than a given small value that is function of said measured flexion according to a function set beforehand, and negative in the opposite case.

10. Use of a sensor according to any of the previous points, said use comprising the steps of
(A) fixating a first and a second ligament-retaining element on a ligament, preferably by sewing;
(B) removing an installing housing and/or a fixating pin if said installing housing and/or said fixating pin is present;
(C) attaching a wire to said sensor by attaching a wire-relating mechanical connector to a sensor-relating mechanical connector;
(D) calibrating said sensor by means of a calibration means if said calibration means is present;
(E) measuring a difference between a strain in said ligament at a first point in time and said strain at a second point in time.

11. A computer program product for use in a computer device belonging to a system according to any of the points 8 or 9, said computer program product including a plurality of computer executable instructions stored on a computer readable medium, wherein said computer comprises a display, wherein said instructions, when executed by said computer device, cause the computer device to perform the steps of:
(I) receiving a conditioned signal comprising a strain-indicating parameter from a computer bus of a data acquisition module,
(II) processing said conditioned signal according to a plurality of processing purposes, including any or any combination of the following: calculation of a statistical quantity relating to said strain-indicating parameter, visualization of a diagram relating to said strain-indicating parameter, configuration of a system parameter relating to said sensor unit and/or said signal conditioning unit;
(III) optionally, receiving a measurement of a sensing parameter from a multipurpose sensing module via a sensing network interface, preferably according to a wireless protocol, more preferably Wi-Fi or ZigBee or Wireless USB, most preferably Bluetooth;
(IV) optionally, deriving a flexion of a knee of a patient from said sensing parameter,
(V) optionally, process said sensing parameter and/or said flexion according to a plurality of processing purposes, including any or any combination of the following: calculation of a statistical quantity relating to said sensing parameter and/or said flexion, visualization of a diagram relating to said sensing parameter and/or said flexion, configuration of a system parameter relating to said multipurpose sensing module;
(VI) showing said processed conditioned signal and optionally said processed sensing parameter on said display;

12. A kit comprising kit elements for mounting a device according to any the points 1 to 7, said kit comprising a sensor, comprising a sensor-relating mechanical connector;
at least one patient-specific wire kit, said patient-specific wire kit comprising a first ligament-retaining element; a second ligament-retaining element; a wire; a bridging element; a wire-relating mechanical connector; optionally, an installing housing; optionally, a fixating pin;
whereby said wire comprises a proximal wire portion near said proximal end of said wire guiding channel and whereby said proximal wire portion is optionally enveloped by said installing housing, optionally held in place by said fixating pin;
whereby said sensor-relating mechanical connector and said wire-relating mechanical connector are adapted for mutual and reversible attachment, preferably screwing or clipping.

13. A kit comprising
a building kit according to point 12;
a knee prosthesis adapted for total knee arthroplasty.

14. A method for using a kit according to any of the points 12 to 13, said method comprising the steps of
(a) fixating a first and a second ligament-retaining element on a ligament, preferably by sewing;
(b) removing an installing housing and/or a fixating pin if said installing housing and/or said fixating pin is present;
(c) attaching a wire to a sensor by attaching a wire-relating mechanical connector to a sensor-relating mechanical connector;
(d) calibrating said sensor by means of a calibration means if said calibration means is present;
(e) measuring a difference between a strain in said ligament at a first point in time and said strain at a second point in time.

15. A method for evaluating the positioning of a knee prosthesis of a patient, said method comprising the steps of
(i) fastening a wire on a first ligament-retaining element, preferably by gluing;
(ii) guiding said wire through a wire guiding channel of a bridging element, said bridging element comprising a distal end, a proximal end and said wire guiding channel for guiding said wire essentially between said distal end and said proximal end;
(iii) fastening said distal end of said bridging element on a second ligament-retaining element, preferably by gluing;
(iv) fixating said first and said second ligament-retaining element on a ligament of said patient, preferably by sewing;
(v) attaching said wire to a sensor by attaching a wire-relating mechanical connector to a sensor-relating mechanical connector attached to said sensor, whereby said sensor is configured to measure a strain-indicating parameter representing a position of said wire relative to the proximal end of the bridging element for obtaining a difference between a strain in said ligament at a first point in time and a strain at a second point in time;
(vi) calibrating said sensor by means of a calibration means if said calibration means is present;
(vii) measuring a native strain in said ligament by means of said sensor, a signal conditioning unit, a computer device, and optionally measuring a flexion and/or a sensing parameter associated with said native strain by means of an optional multipurpose sensing unit;
(viii) positioning said knee prosthesis;
(ix) evaluating the positioning of said knee prosthesis at a current point in time by measuring the difference between said native strain in said ligament and a strain at said current point in time; optionally taking into account a flexion and/or a sensing parameter associated with said current point in time; whereby said evaluating of the positioning is positive if said difference is smaller than a given small value set beforehand causing the method to end, and negative in the opposite case causing a return to step (viii).

In a further embodiment relating to the integrated device according to the present invention, the ligament-attaching element may be the same as the first ligament-retaining element according to the present invention, but may also differ from it. Furthermore, the slider housing may comprise a bridging element that forms an extension of the slider guiding channel, the bridging element thereby extending between the slider housing and the ligament-attaching element. In a further related embodiment, said slider is a wire, and the fixation point of the slider module to the ligament is situated at a distal end of said bridging element. In another preferred embodiment, the device according to the present invention comprises a Hall sensor. In this regard, there is not always any difference between an embodiment of the integrated device and an embodiment of the device according to the present invention.

In a preferred embodiment of the integrated device according to the present invention, said slider module comprises a slider housing and a slider head; said slider housing comprising said slider guiding channel and said sensor; said slider head comprising a piece of ferromagnetic material comprising at least one magnetic pole pair, preferably a magnet; wherein said slider head and said slider housing are adapted for sliding of said slider head within said slider housing, wherein said proximal slider end is attached to said slider head, and wherein said Hall sensor is configured for converting a position of said piece of ferromagnetic material into said measurement of said strain-indicating parameter. This has the advantage of yielding a robust and accurate measurement instrument.

In a preferred embodiment of the integrated device according to the present invention, said sensor comprises two or more Hall sensors, preferably linear Hall sensors, configured such that said Hall sensor is essentially sensitive to a magnetic field variation along a single axis only, said single axis essentially coinciding with a path of said piece of ferromagnetic material during said sliding.

In a preferred embodiment of the integrated device according to the present invention, said sensor comprises a Hall sensor array comprising a plurality of Hall sensors, and whereby said piece of ferromagnetic material comprises a plurality of magnetic pole pairs.

In a preferred embodiment of the integrated device according to the present invention, said slider comprises an elongated strip and/or wire comprising an essentially non-magnetic material with low deformation under tensile stress and/or compressive stress and/or bending, preferably biocompatible polyimide, nylon and/or a non-magnetic biocompatible metal such as nitinol.

In a preferred embodiment of the integrated device according to the present invention, said ligament-attaching element and said slider module are adapted to be fastened on said ligament by sewing, preferably through the use of sewing thread, preferably biocompatible sewing thread.

In a preferred embodiment of the integrated device according to the present invention, ligament-attaching element and said slider module are adapted to be fastened on said ligament by any or any combination of the following: dry glue, preferably synthetic setae, more preferably gecko tape/glue; micro-needles, preferably swellable-tip micro-needles. Furthermore, this may be combined with or replaced by sealing. Said type of fastening is advantageous since it allows attachment with minimal risk of damage to the ligament.

In a preferred embodiment, said device comprises a clamping mechanism for preventing damage during transport. Such a clamping mechanism may block or reduce the movement of portions of the device when not used. The clamping mechanism is to be released before use of the device.

As mentioned above, in a preferred embodiment of the integrated device according to the present invention, said integrated device further comprises a transmitter module, preferably a low-power transmitter module, said transmitter module configured to transmit said measurement of said strain-indicating parameter to a computer device, preferably according to a wireless protocol, more preferably Wi-Fi or ZigBee or Wireless USB, most preferably Bluetooth, and whereby said integrated device comprises a power source, preferably a battery, whereby said integrated device is adapted to operate entirely within a sterile zone in close proximity to said ligament, without any cable going beyond said sterile zone. This allows implementation of the entire device as a sterile, stand-alone patch. This patch can be attached for knee surgery for instance according to following procedure comprising two phases. In a first of said two phases, the attachment procedure, the leg cannot be moved. The first phase comprising following steps: attach ligament-attaching element and slider module onto the ligament; attach transmitter module with sticker on the lower back of the lower leg; release clamping mechanism; establish communication between transmitter module and said computer device. In a second of said two phases, the leg can be moved. The second phase comprises performing consecutive measurements during surgery.

In a preferred embodiment of the integrated device according to the present invention, said transmitter module comprises an integrated sensing module for measuring a sensing parameter, said transmitter module configured to transmit said measurement of said sensing parameter to said computer device, and whereby said integrated sensing module comprises any or any of the following: an accelerometer, preferably a 3-axis accelerometer; a gyroscope; a magnetometer; a positioning meter. This integrated sensing module has similar advantages as the multipurpose sensing module according to the present invention.

In a preferred embodiment of the integrated device according to the present invention, said ligament-attaching element and said slider module are adapted to be attached to said ligament belonging to a knee belonging to a leg of a patient, and whereby said transmitter module is adapted to be attached to a tibia belonging to said leg of said patient.

In a preferred embodiment of the integrated device according to the present invention, said integrated device is adapted to be sterilized, said integrated device comprising an OFF-mode for preventing battery drain during storage and battery-relating damage to said integrated device due to sterilizing. The latter is advantageous since it is known that sterilizing may result in undesired electrical effects if the device components are powered during sterilization. In a preferred embodiment, the device is adapted for sterilization by any or any combination of sterilization relating to gamma ray, electron beam, X-ray, autoclave, ethylene oxide, chlorine dioxide gas. Hereby, preferably, the device housing is adapted to resist to the severe conditions involved in sterilizing.

The invention is further described by the following non-limiting examples which further illustrate the invention, and are not intended to, nor should they be interpreted to, limit the scope of the invention.

EXAMPLES

Example 1: First Embodiment According to the Present Invention

FIG. 1 shows a first embodiment according to the present invention. Particularly, the figure shows a device 1 suitable for measuring the difference between a strain in a ligament at a first point in time and said strain at a second point in time. A first ligament-retaining element 2 and a second ligament-retaining element 3 have a shape and dimensions suitable for being fastened on said ligament close to each other.

Specifically, FIG. 1 shows the front of said first ligament-retaining element. Said first ligament-retaining element has a front width of about 4 mm along a width direction essentially parallel to the wire. Said first ligament-retaining element has a front height of about 10 mm along a height direction essentially perpendicular to said width direction. Said first ligament-retaining element has a depth of about 2 mm along a depth direction (not shown on FIG. 1) essentially perpendicular to said width direction and essentially perpendicular to said height direction. Said front comprises four cut-outs (counterpart to 21-24 in FIGS. 2 and 3) extending along said depth direction. Said cut-outs are adapted for receiving sewing thread 4. Similarly, said second ligament-retaining element of which the front is shown on FIG. 1 comprises four cut-outs (counterpart to 31-34 in FIGS. 2 and 3) extending along said depth direction, equally adapted for receiving sewing thread 4. For the embodiment shown on FIG. 1, said first and said second ligament-retaining element are identical, having equal dimensions and shape. In an alternative and preferred embodiment, said first ligament-retaining element and said second ligament-retaining element differ in shape and/or size. Furthermore, for the embodiment shown on FIG. 1, sewing thread 4, preferably biocompatible sewing thread, is used to fasten both ligament-retaining elements 2 and 3. Upon fastening, the spacing between a left outer end of said first ligament-retaining element and a right outer end of said second ligament-retaining element is about 25 mm and not smaller than 20 mm. The actual spacing varies according to the strain in said ligament; however, one may define a "native spacing". Said "native spacing" is fixed on the moment that a wire and a bridging element 6 are fastened on said first and said second ligament-retaining element, respectively. Hereby, said bridging element 6 comprises a distal end 61, a proximal end 62 and a wire guiding channel 63 for guiding said wire 5 between said distal end 61 and said proximal end 62. Hereby, it is said distal end 61 that is fastened on said second ligament-retaining element 3, in a preferred embodiment by gluing. To facilitate said gluing, said first ligament-retaining element 2 comprises a first groove (counterpart to 25 in FIGS. 2 and 3) along said width direction, allowing for reliable gluing of said outer end of said distal wire portion 51 to said first ligament-retaining element 2. Analogously, said wire 5 comprises a proximal wire portion 52 near said proximal end 62 and a distal wire portion 51 near said distal end 61. Hereby, it is the outer end of said distal wire portion 51 that is fastened on said first ligament-retaining element 2, in a preferred embodiment by gluing. Also here, to facilitate said gluing, said second ligament-retaining element 3 comprises a second groove (counterpart to 35 in FIGS. 2 and 3) along said width direction, allowing for reliable gluing of said outer end of said distal end 61 to said second ligament-retaining element 3.

In their combination, said ligament-retaining elements 2 and 3, said bridging element 6 and said wire 5 allow to translate strains in said ligament into relative motion of said distal wire portion 51 with respect to said distal end 61, which are transferred unchangingly to relative motion of said proximal wire portion 52 with respect to said proximal end 62. This is a useful feature of said device, since it allows to measure strain of the ligament from a remote point rather than measuring strain immediately on the ligament.

Said relative motion of said proximal wire portion 52 with respect to said proximal end 62 is measured by a sensor 71 belonging to a sensor unit 7. In a preferred embodiment, said sensor is a transducer, preferably comprising a linear variable differential transformer. In a preferred embodiment, said sensor is attached to said proximal end 62 of said wire guiding channel 63, preferably enveloping said wire guiding channel 63, and this without touching said proximal wire portion 52 present in the wire guiding channel 63. Said sensor is able to measure the relative position and/or motion of said proximal wire portion 52 with respect to said proximal end 62 by measuring the electromagnetic response of said proximal wire portion 52. To this end, the outer end 53 of said proximal wire portion 52 is preferably composed of a ferromagnetic material, more preferably metal. Furthermore, said proximal wire section 52 and said wire 5 are connected via a spacer wire section 301 that is composed of a material with low electrical conductivity, preferably an electrically insulating material, more preferably electrically insulating plastic.

Apart from said sensor 71, said sensor unit 7 comprises an inner housing 72, said inner housing enveloping said sensor 71. In its turn, said inner housing 72 is enveloped by an outer housing 73.

Said inner housing 72 comprises an inner housing shell 721 enveloping said sensor 71; a calibration screw 722 for positioning said sensor 71; optionally a small calibration cut-out 723 in the outer surface of said inner housing 72 for receiving an outer end of said calibration screw 722, allowing accurate positioning of said inner housing 72 by means of said calibration screw 722; a calibration spring 724 for keeping in place said inner housing 72, allowing further accurate positioning of said inner housing 72; an inner housing cut-out 725 for receiving said bridging element 6.

Said outer housing 73 comprises an outer housing shell 731 enveloping said inner housing 72; a sensor-relating guide piece 732 for guiding said bridging element 6 toward said sensor 71; an outer housing cut-out 733 for receiving said sensor-relating guide piece 732. Hereby, said sensor-relating guide piece 732 comprises a sensor-relating mechanical connector 7321 at its outer end pointing outward with respect to said outer housing 73. In a preferred embodiment, said sensor-relating mechanical connector 7321 is an adaptation to the surface of said sensor-relating guide piece 732 suitable for realizing a mechanical connection, such as screw thread.

Furthermore, said device 1 comprises a wire-relating mechanical connector 8 attached on said bridging element 6 and preferably enveloping said bridging element 6. Said wire-relating mechanical connector 8 is adapted for mutual and reversible attachment with said sensor-relating mechanical connector 7321, preferably by screwing or clipping, more preferably by screwing. In a preferred embodiment, said wire-relating mechanical connector 8 comprises an inner connector part 81 attached to said bridging element 6 as well as an outer connector part 82 enveloping said inner connector part 81, whereby said outer connector part 82 is adapted for pivoting around said inner connector part 81.

In their combination, said inner housing 72 and said outer housing 73 and all their comprised elements are able to measure a position said proximal wire portion 52 with respect to said proximal end 62. Correspondingly, said device 1 allows for measuring the difference between a strain in a ligament at a first point in time and said strain at a second point in time.

In a preferred embodiment, said sensor 71 comprises sensor-relating calibration means to ensure a desired position of said sensor 71 relative to said wire 5. Preferably, the desired position of said sensor 71 with respect to said wire 5 is concentric. In an alternative embodiment, said sensor-relating calibration means are easily controllable in real-time or near-real-time, and said desired position is not concentric but slightly eccentric. Hereby, the desired position is determined such that said wire 5 is mechanically clamped by said sensor 71, whereby said clamping limits the relative movement of the wire 5 with respect to the sensor 71 without completely inhibiting said relative movement. Hereby, the aim of said clamping is to create a limited and controllable amount of strain on the ligament. This, in its turn, allows to measure ligament slackness, whereby said sensor-relating calibration means constitutes an actuator, complementary to the actuator discussed in Example 5 below.

Example 2: Second Embodiment According to the Present Invention

Figure 2:
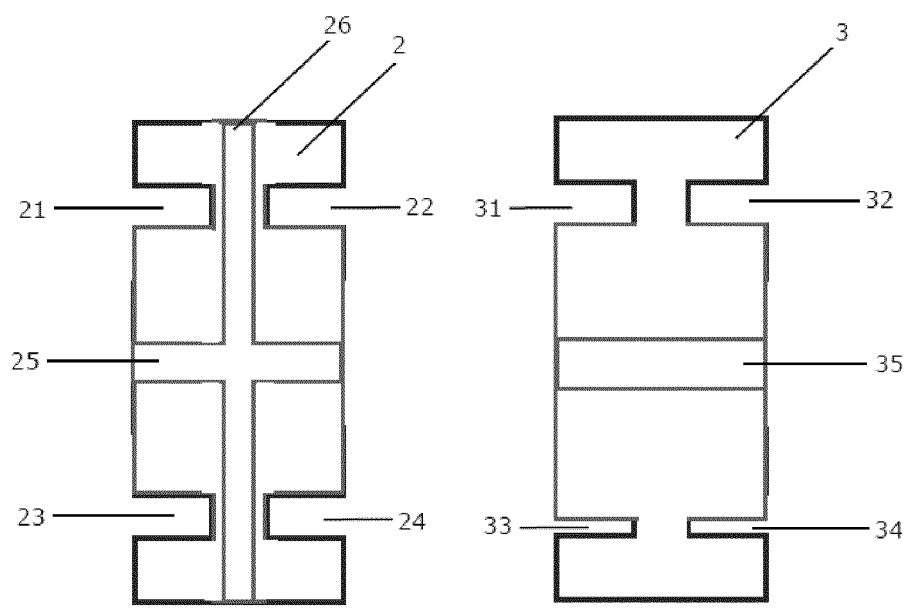
FIG. 2 shows a first view of a second embodiment according to the present invention.
Figure 3:
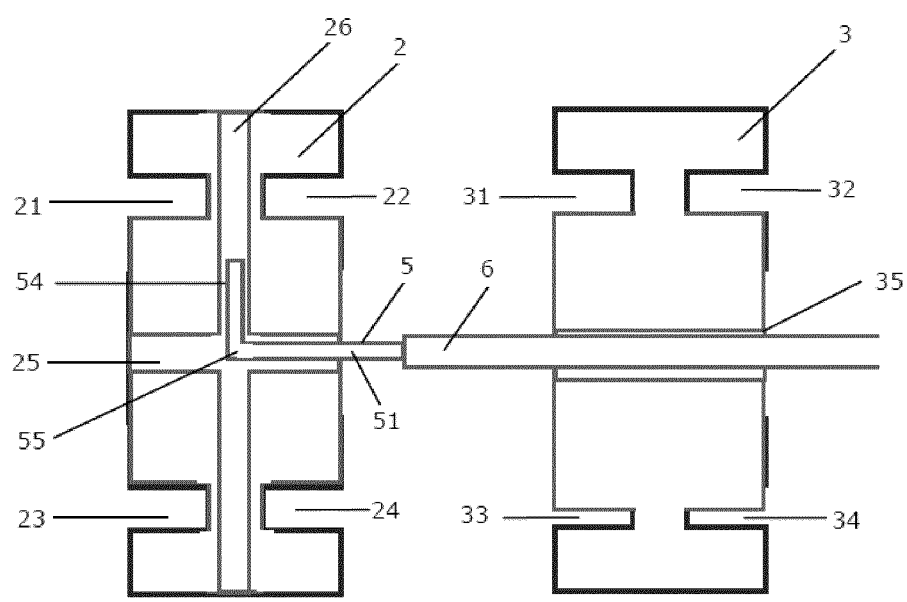
FIG. 3 shows a second view of a second embodiment according to the present invention.

The second embodiment according to the present invention is illustrated in FIGS. 2 and 3. Both figures show a second embodiment of said first and second ligament-retaining element 2 and 3, respectively. Similar as in the first embodiment, to facilitate gluing of the outer end of said distal wire portion 51 to said first ligament-retaining element 2, said first ligament-retaining element 2 comprises a first groove 25 along a width direction.

Similar as in the first embodiment, to facilitate gluing of said distal end 61 to said second ligament-retaining element 3, said second ligament-retaining element 3 comprises a second groove 35 along said width direction. In an alternative embodiment (not shown in the figures), the second ligament-retaining element does not comprise a second groove 35 but instead a hole to facilitate gluing of said distal end 61 to said second ligament-retaining element 3. Hereby, said hole extends along said width direction over the full width of said second ligament-retaining element. Said hole, preferably with circular cross-section, is adapted in diameter to receive said distal end 61. In a preferred embodiment, said distal end 61 is glued to said second ligament-retaining element 3, whereby glue attached said distal end 61 to the surface of the hole.

Similar as in the first embodiment, the front of said first and second ligament-retaining element 2 and 3 comprises four cut-outs 21-24 and 31-34 respectively, extending along said depth direction.

Different from the first embodiment, in the present second embodiment, the first ligament-retaining element 2 further comprises a locking groove 26 in a direction orthogonal to said wire guiding channel. Said locking groove further improves the quality of the fastening of said wire 5 to said first ligament-retaining element 2. More precisely, by positioning the outer end 54 of said wire 5 in said locking groove 26 and bending said wire 5 in a bending point 55 to further guide said wire 5 along said first wire-guiding-channel-aligned groove 25 and gluing while this position is maintained, a better overall fastening of said wire 5 to said ligament-retaining element 2 is realized.

Example 3: Third Embodiment According to the Present Invention

Figure 4:
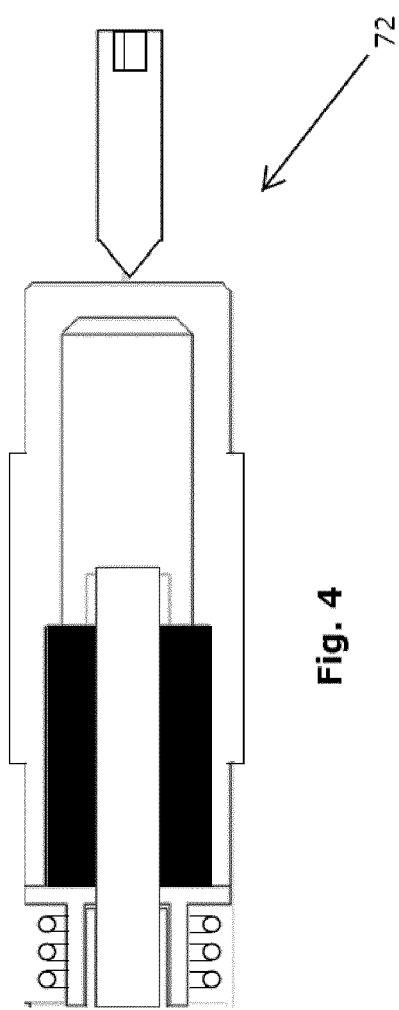
FIG. 4 shows a first view of a third embodiment according to the present invention.
Figure 5:
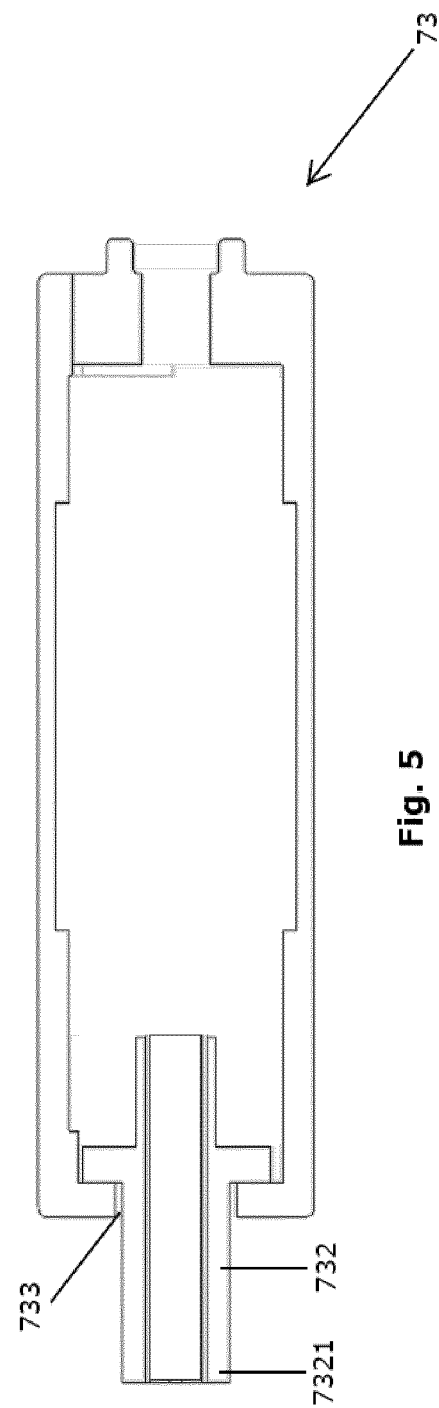
FIG. 5 shows a second view of a third embodiment according to the present invention.
Figure 6:
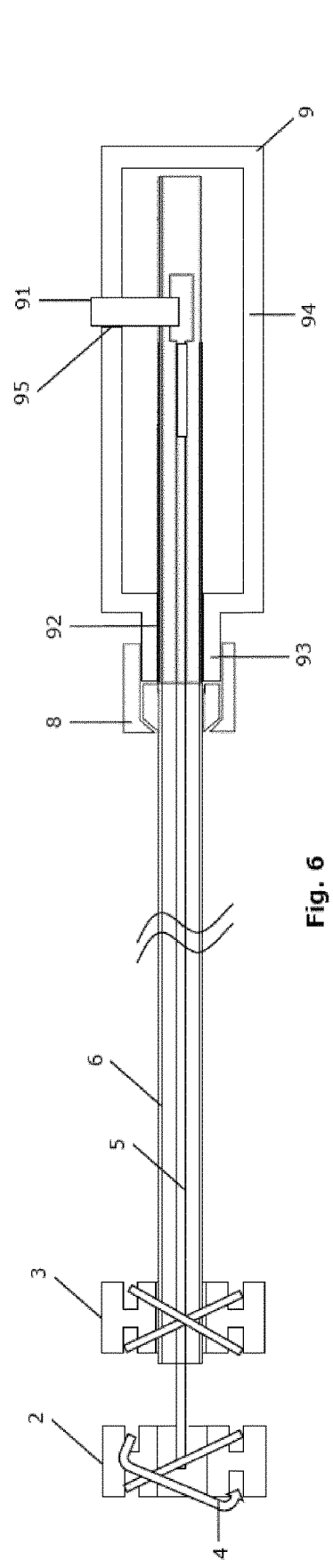
FIG. 6 shows a first view of a fourth embodiment according to the present invention.

The third embodiment according to the present invention is illustrated in FIGS. 4 and 5. It shows the same inner housing 72 and outer housing 73 as in the first embodiment, yet disassembled instead of assembled.

Example 4: Fourth Embodiment According to the Present Invention

The fourth embodiment according to the present invention is illustrated in FIGS. 6 to 9. It illustrates a method for using a device according to the present invention, as well as additional device parts not illustrated in the previous embodiments, including an installing housing 9.

Said installing housing 9 comprises an installing housing shell 94 enveloping said proximal wire section 52; a fixating pin 91 for keeping in place said outer end 53 of said proximal wire section 52; a fixating-relating cut-out 95 for receiving said fixating pin 91; a bridge-element-relating protrusion 92 with a tubular structure for receiving said bridge element 6; an installing-relating mechanical connector 93. In a preferred embodiment, said installing-relating mechanical connector 93 is an adaptation to the surface of said a bridge-element-relating protrusion 92 suitable for realizing a mechanical connection, such as screw thread, adapted for connection with a wire-relating mechanical connector 8 attached on said bridging element 6 and preferably enveloping said bridging element 6. Said wire-relating mechanical connector 8 is adapted for mutual and reversible attachment with said installing-relating mechanical connector 93 as well as said sensor-relating mechanical connector 7321, preferably by screwing or clipping, more preferably by screwing. As in the first embodiment, in a further preferred embodiment, said wire-relating mechanical connector 8 comprises an inner connector part 81 attached to said bridging element 6 as well as an outer connector part 82 enveloping said inner connector part 81, whereby said outer connector part 82 is adapted for pivoting around said inner connector part 81.

Figure 7:
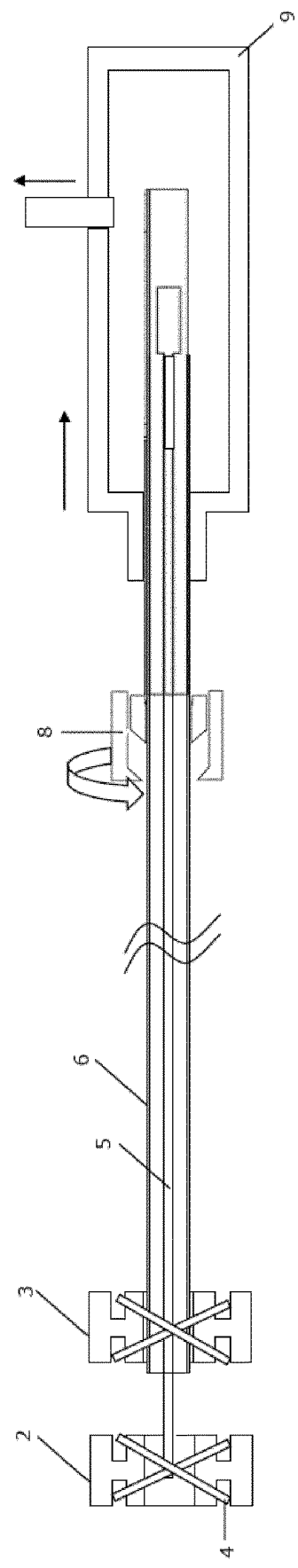
FIG. 7 shows a second view of a fourth embodiment according to the present invention.
Figure 8:
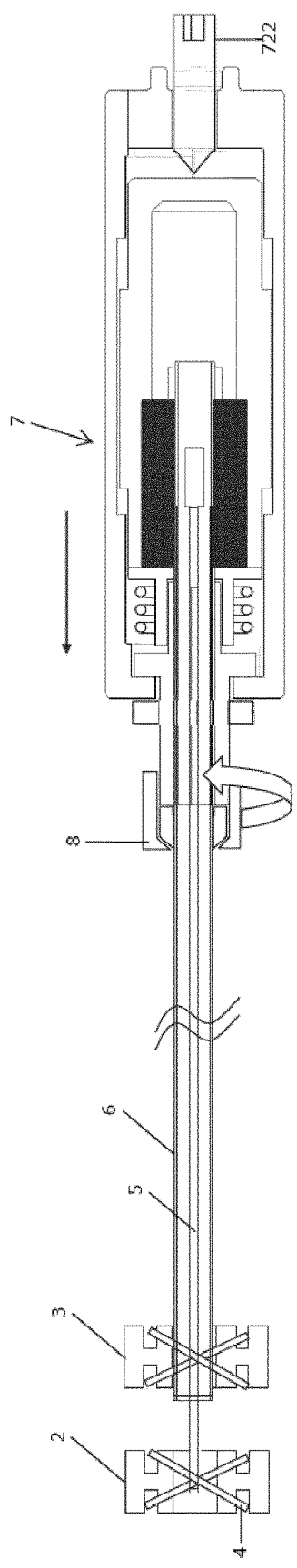
FIG. 8 shows a third view of a fourth embodiment according to the present invention.
Figure 9:
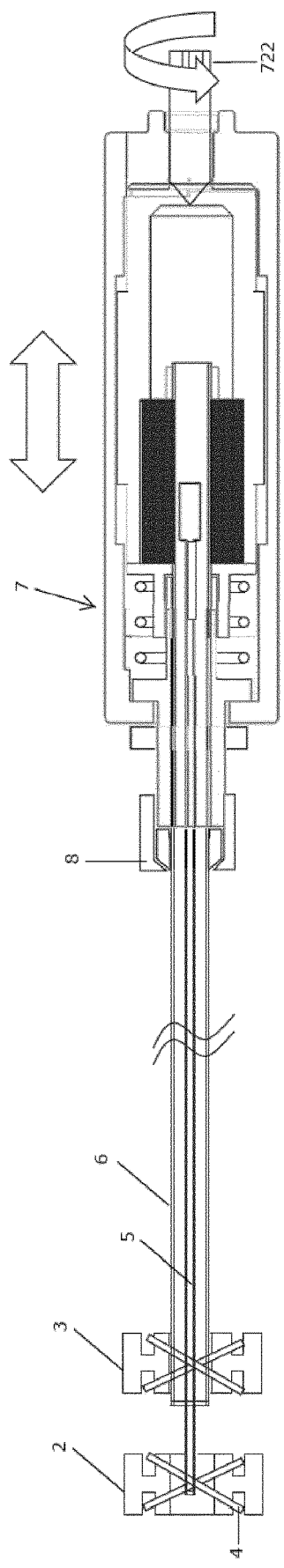
FIG. 9 shows a fourth view of a fourth embodiment according to the present invention.

The method illustrated in FIGS. 6 to 9 comprises 4 steps for installing, calibrating and using a device according to the present invention. Specifically, said method comprises the steps of fixating said first and said second ligament-retaining element on said ligament by sewing, illustrated by FIG. 6;

removing said installing housing and said fixating pin, illustrated by FIG. 7;

attaching said wire to said sensor by attaching said wire-relating mechanical connector to said sensor-relating mechanical connector, illustrated by FIG. 8;

calibrating said sensor by means of said calibration screw 722, illustrated by FIG. 9;

measuring said difference between said strain in said ligament at said first point in time and said strain at said second point in time, as use of a device as illustrated by FIG. 1.

It is supposed that the present invention is not restricted to any form of realization described previously and that some modifications can be added to the presented example of fabrication without reappraisal of the appended claims. For example, the present invention has been described referring to a sensor based on electromagnetic response, but it is clear that the invention can be applied to an optical sensor for instance or to a sensor combining electrical and optical effects.

Example 5: Fifth Embodiment According to the Present Invention

Figure 10:
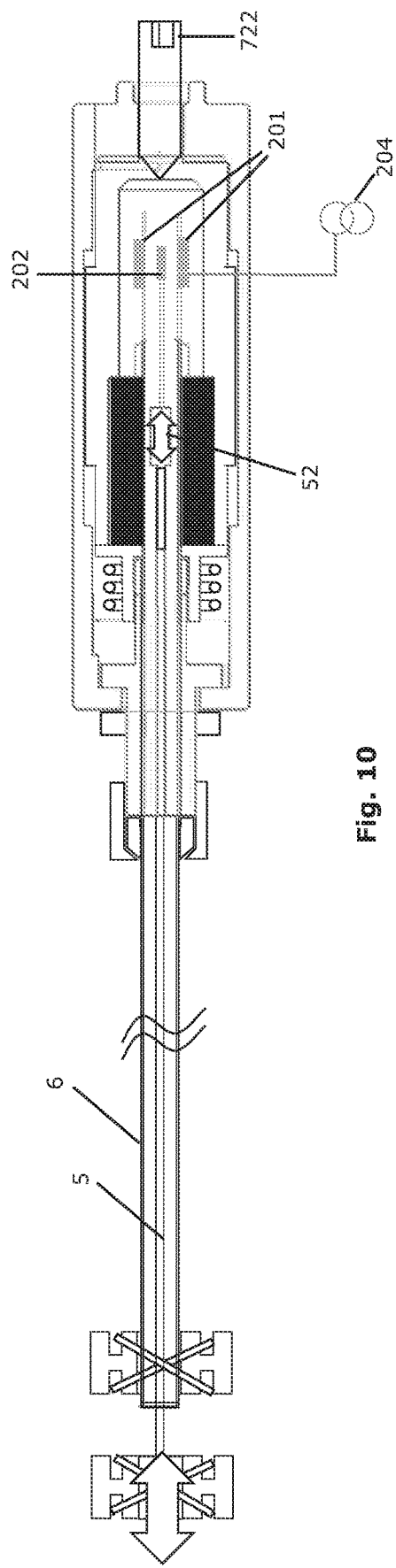
FIG. 10 shows a fifth embodiment according to the present invention.

The fifth embodiment according to the present invention is illustrated in FIG. 10. It illustrates an extension of the device shown in FIG. 1 (first embodiment). In the extension, the bridging element 6 of the first embodiment is elongated in the direction of the calibration screw 722 as indicated. Also the wire 5 is elongated, extending beyond the proximal wire portion 52 of FIG. 1. The wire 5 comprises a small permanent magnet rod 202 attached at its end, whereby the axis connecting the magnet rod's north pole and south pole is directed in parallel to the wire 5. Furthermore, a solenoid or coil of wire 201 is wound around the bridging element near the position of said magnet rod 202. By generating current with an electric modulator 204 connected to both ends of said coil of wire 201, a magnetic field is generated within the coil, exerting a force on said magnet rod 202 along a direction parallel to the wire 5. Hereby, the orientation of said force, i.e. a force pointing toward the calibrator screw 722 or away from it, depends on the polarity of the electric modulator 204 and the orientation of the magnetic rod 202. This results in a device that has actuator functionality on top of sensor functionality. In a preferred embodiment, the modulator 204 generates a direct current (DC). Said modulator is able to switch the direction of the current, allowing to switch the direction of said force. The amplitude of the force is proportional to the amount of current running through the coil of wire 202. The force exerted on the magnetic rod is transferred to the ligament via said wire 5. The resulting displacement is measured by the sensor. This allows to quantify the slackness of the ligament, which is an important second parameter characterizing ligament conditions, apart from ligament strain. Particularly, knowledge of the sensor measurements together with the currents generated by the modulator allows to derive values for the ligament strain as well as the ligament slackness. In a preferred embodiment, the sample rate of the sensor is at 10 measurements per second; in a more preferred embodiment, the sample rate of the sensor is higher, to up to 1000 measurements per second. This allows a fast response and measurement, whereby the actuator can be moved relative rapidly. In an alternative embodiment, said permanent magnet rod 202 is replaced by a portion of any other material susceptible to variations in a magnetic field, such as a ferromagnetic, paramagnetic or diamagnetic material.

Example 6: Sixth Embodiment According to the Present Invention

Figure 11:
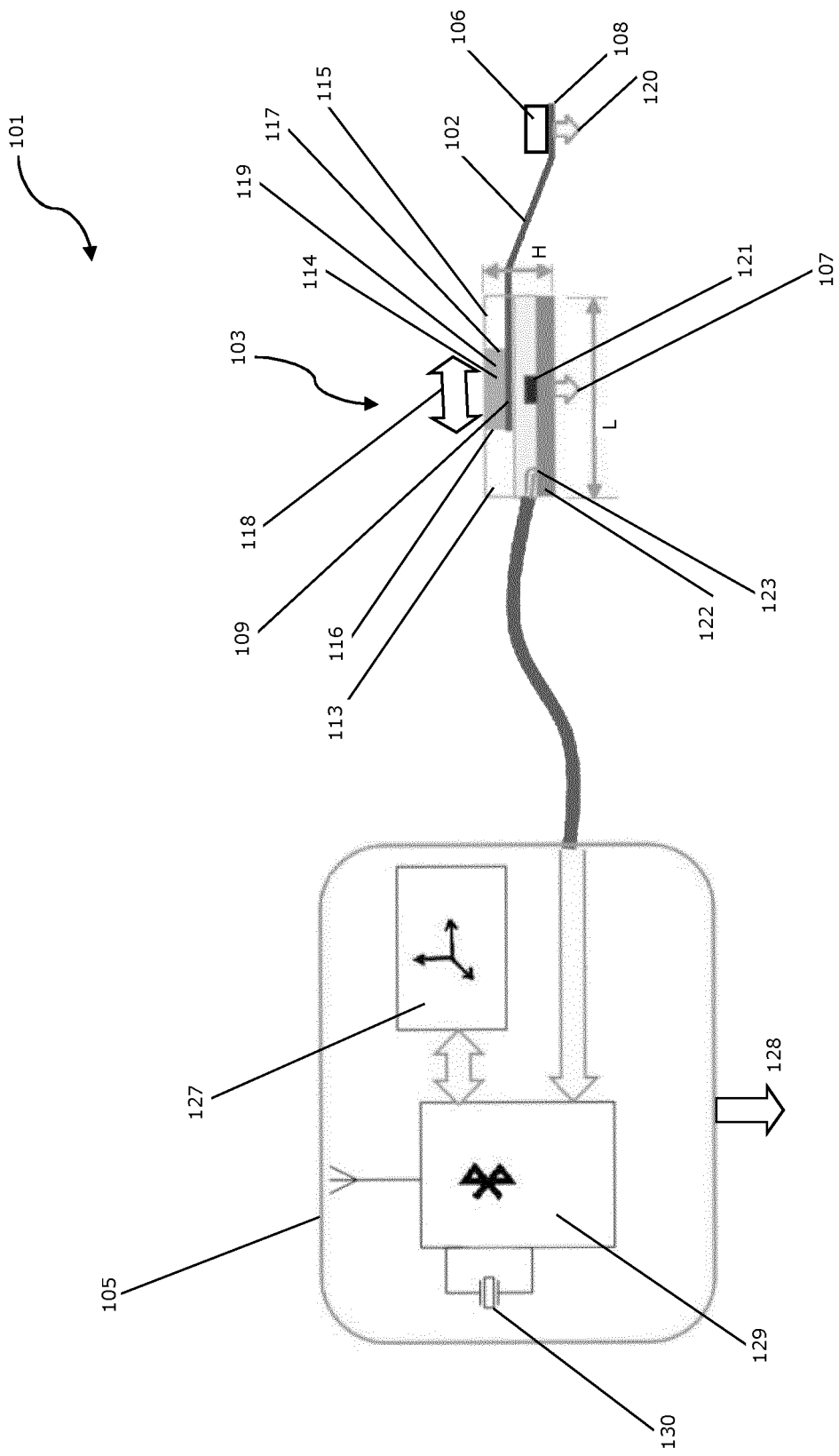
FIG. 11 shows a sixth embodiment according to the present invention (first view).

The sixth embodiment according to the present invention is illustrated in FIG. 11, and relates to an integrated device 101. Said integrated device comprises a slider 102 and a slider module 103 that are displayed in FIG. 11 in a side view. Said integrated device further comprises a transmitter module 105 connected to said slider module 103 with a cable 104 with electric wiring.

The slider, in this example essentially an elongate strip with width dimension along the depth direction of FIG. 11 (not shown), comprises a distal slider end 108 and a proximal slider end 109. The distal slider end 108 comprises a ligament-attaching element 106 for attaching the slider 102 to a ligament 112 of a knee 111 of a patient at a first fixation point 120, preferably by dry gluing. The slider module 107 can also be attached at a second ligament fixation point 107 to the ligament 112, also preferably by dry gluing. In a preferred embodiment, the height H of the slider module 103 is 3 to 4 mm, and the length L of the slider module is 10 to 12 mm. The slider module comprises a slider housing 113 and a slider head 119, said slider head 119 comprising a magnet 114 comprising a magnetic North-South pole pair. The magnetic pole pair comprises a first pole at a first magnet end 116 and a second pole at a second magnet end 117. Said slider housing comprises a slider guiding channel 115; said slider head and said slider guiding channel 115 are adapted to allow movement of said slider head within said slider guiding channel 115 along a sliding direction 118. Said slider head 119 is attached to the proximal end 109 of said slider 102. Furthermore, the slider housing comprises a printed circuit board (PCB) 122 and a Hall sensor 121 in a sealed area. The Hall sensor 121 is mounted on said PCB 122, which is connected via a wire contact area 123 with said cable 104, which in turn connects to the rest of the integrated device 101, i.e. the transmitter module 105. The Hall sensor 121 is placed in close proximity to slider guiding channel 115 and the magnet 114 without contacting either of them.

The operation of the integrated device is as follows. The aim of the device is to measure the strain in the ligament 112 by measuring the relative distance between the first fixation point 120 and the second fixation point 107. Hereby, the first fixation point 120 is attached fixedly to a first portion of the ligament 112, and therefore, the slider 102 and the ligament-attaching element 106 move along with this first portion as it changes position, e.g. during the positioning of a knee prosthesis (124 and 125). Likewise, the second fixation point 120 and also the slider module 103 move along with a second portion of the ligament 112 near said first portion and located closer to the tibia 126 of the patient. Summarizing, the slider 102 copies the movement of the first fixation point 120 while the slider module 103 copies that of the second fixation point. As a result, measuring the relative movement of the slider 102 in the slider guiding channel 115 by means of said Hall sensor 121 that moves along with the slider module 103 allows to measure strain differences in the ligament 112.

During measurement, the Hall sensor 121 generates a conditioned digital signal comprising the strain-indicating parameter, i.e. the position of the magnet 114 relative to the Hall sensor 121. This signal is carried over via the cable 104 to the transmitter module 105.

The transmitter module 105 is to be attached to the tibia 126 of the patient at an attachment point 128. This attachment is a simple attachment on skin, and does not involve an incision. The transmitter module 105 comprises an integrated sensing module, in this example an accelerometer 127, a control module 129, and a battery 130. This accelerometer 127 measures the acceleration and therefore also the movement and position of the tibia. The role of the accelerometer 127 is to derive flexions of the knee 111 and related information, analogous to an accelerometer belonging to a multipurpose sensing module according to the present invention. Both the cable 104 and the accelerometer 127 are connected to the control module 129 which processes measurements originating from both the Hall sensor 121 and the accelerometer 127. Furthermore, the control unit comprises a battery 130 that powers not only the control unit 129 but the entire integrated device 101. Additionally, the control unit comprises a wireless interface, in this example a Bluetooth interface that allows to transfer measurements originating from the Hall sensor 121 and the accelerometer 127 to a computer device. Since both the power and the data transfer are implemented without wire, the integrated device can be used "wirelessly", in the sense that no cables other than the cable 104 are involved. The computer device (not shown) allows to visualize the evolution of ligament strain during positioning of a knee prosthesis. In the example, the device is conceived as a single-use device, and therefore, a small battery suffices, resulting in overall small footprint for the transmitter module 105 and the integrated device 101 as a whole.

Figure 12:
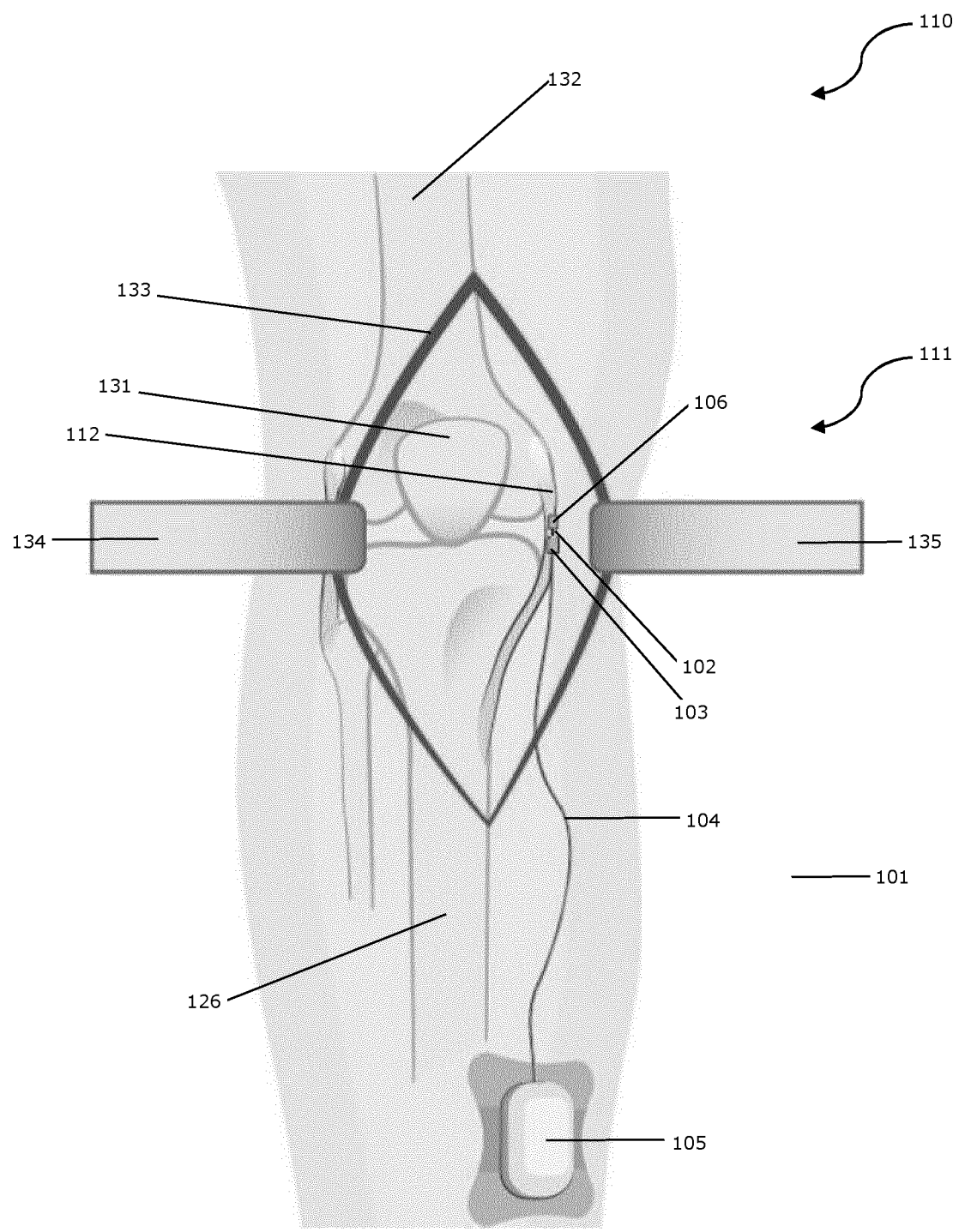
FIG. 12 shows a sixth embodiment according to the present invention (second view).
Figure 13:
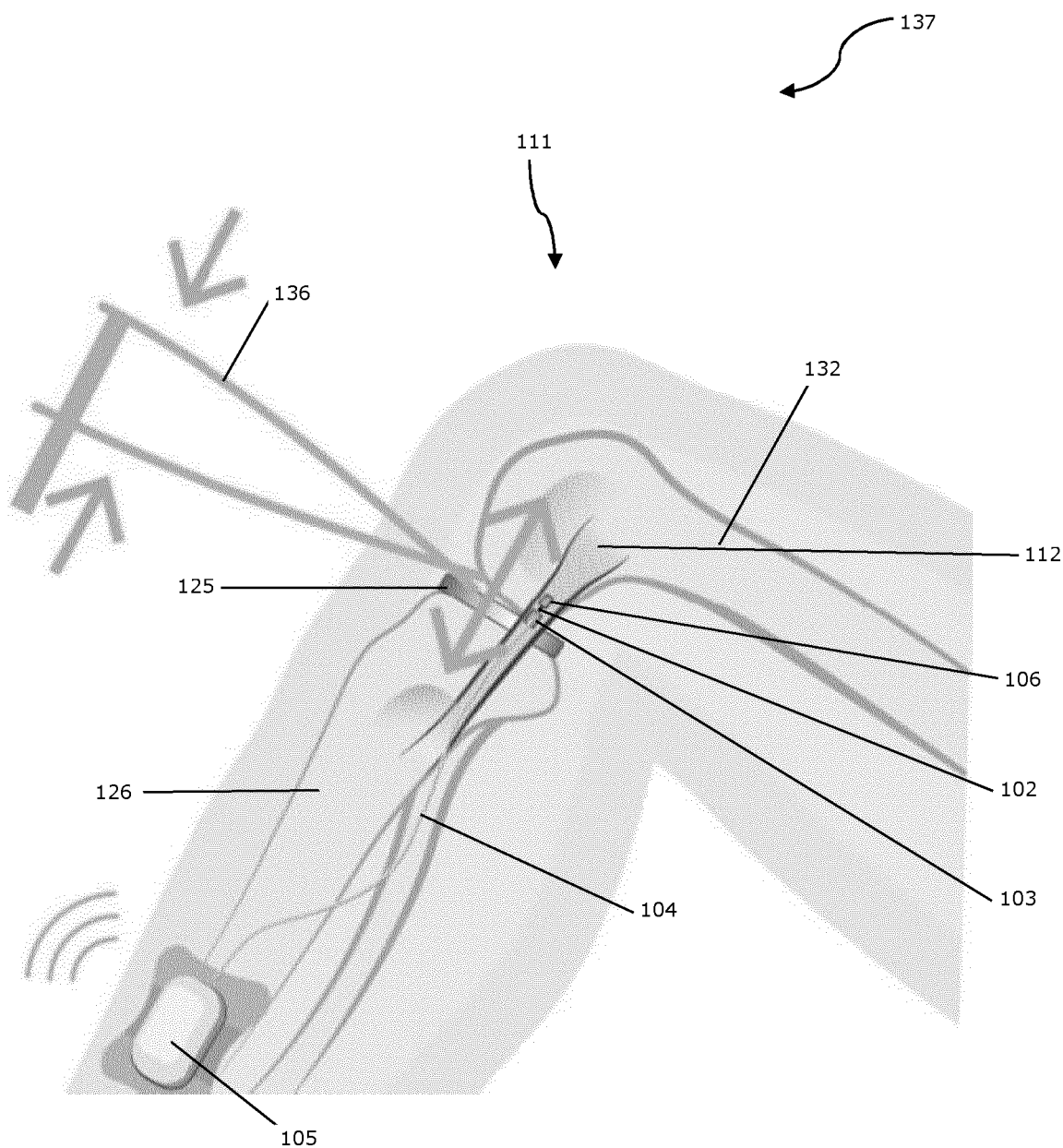
FIG. 13 shows a sixth embodiment according to the present invention (third view).
Figure 14:
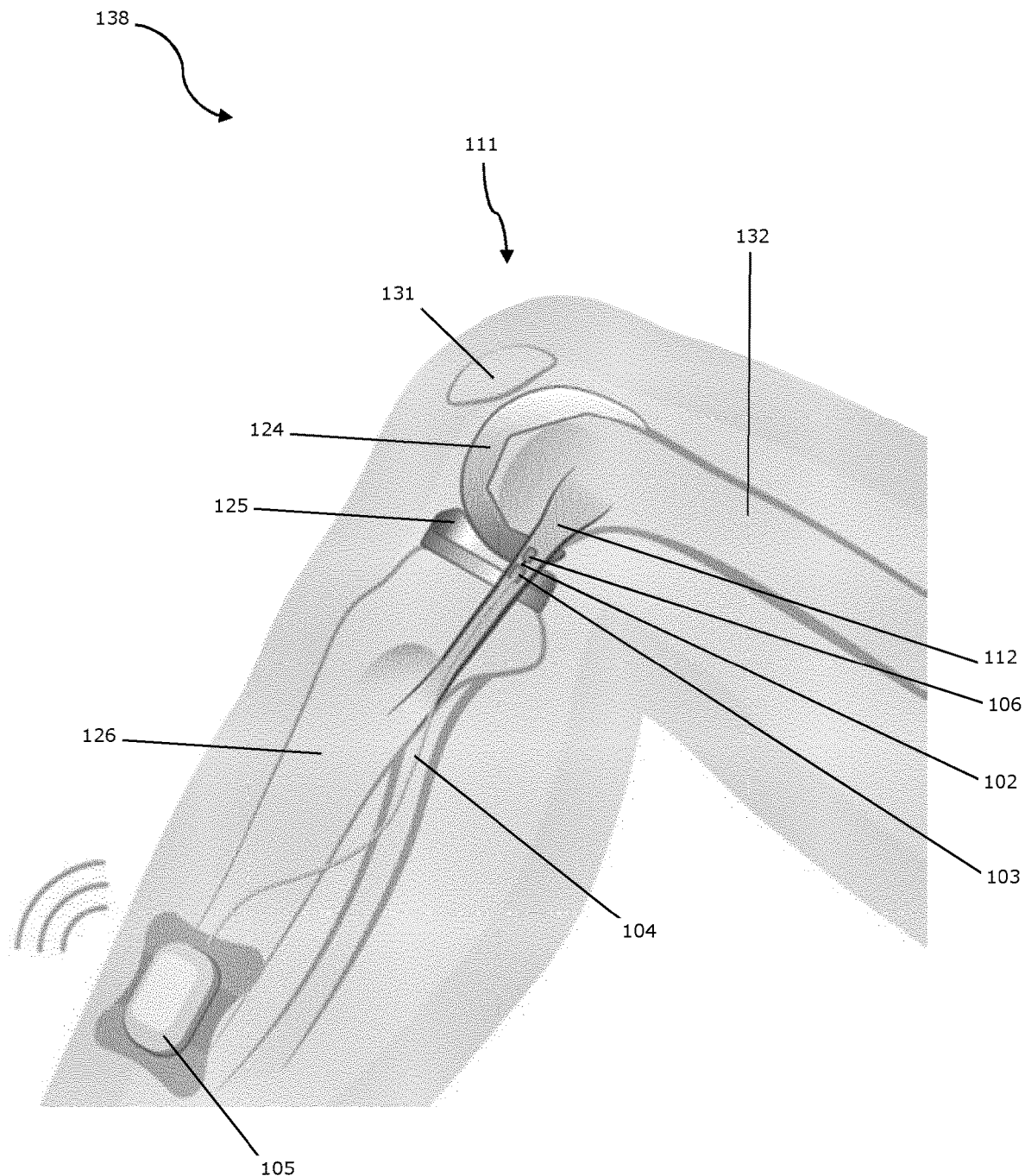
FIG. 14 shows a sixth embodiment according to the present invention (fourth view).

FIGS. 12 to 14 show the typical steps in the positioning of a knee prosthesis (124 and 125) in the knee 111 of a patient. Particularly, the figures show the right knee 111 with the patella 131, femur 132 and tibia 126 before (FIG. 12), during (FIG. 13) and after (FIG. 14) positioning of a knee prosthesis (124 and 125). Hereby, the knee prosthesis comprises an upper part 124 for attachment to the femur 132 and a lower part 125 for attachment to the tibia. The ligament strain is measured on the medial collateral ligament 112.

FIG. 12 illustrates the whole 110 of the integrated device 101 as attached to the knee 111 of a patient, and this before the positioning of a knee prosthesis. The medial lateral ligament 112 is exposed through an incision 133 in the skin. The skin opening is held open with a first and second surgical tool (134 and 135). The incision 133 and the first and second surgical tool (134 and 135) are not shown on FIGS. 11 and 12 for simplicity but are also assumed to be present. After the incision, the integrated device is simply attached to the ligament 112 at the first and second fixation point (107 and 128). Furthermore, the transmitter module is attached on the skin covering the tibia 126.

FIG. 13 illustrates the whole 137 of the integrated device 101 as attached to the knee 111 of the patient during the positioning of the knee prosthesis. At this point, the tibial cut is made (not shown) and a portion of the lower part 125 of the knee prosthesis is already present on the tibia 126. In an alternative embodiment (not shown), the lower part of the knee prosthesis is a small plate. In another alternative embodiment (not shown), the knee prosthesis does not comprise a lower part. The surgeon then uses a balancing tool 136 for determining the positioning of the knee prosthesis (124 and 125). Hereby, the balancing tool may concern, e.g., a Stryker patella in place balancer, a Ferrari tool with inserts of varying thickness, a patella in place lamina spreader, or a tibia first balancer. During the entire positioning procedure, ligament length changes are measured by the integrated device 101 in micrometer precision and are shown on a display of the computer device (not shown). Values are shown and stored on screen while performing varus/valgus laxity tests in both 90° flexion and extension. The surgeon uses this quantified measurement to decide on the femoral cuts, and thus the prosthesis positioning.

FIG. 14 illustrates the whole 138 of the integrated device 101 as attached to the knee 111 of the patient just after the positioning of the knee prosthesis. Now, the entire lower part 125 of the knee prosthesis is present, as well as the upper part 124.

Example 7: Example with Hall Sensors

In this example embodiment, the sensor of said integrated device comprises two Hall sensors. A combination of two AS5510 Hall sensors is used, each with 10 bit precision. The output of the sensor is essentially linear for position differences over a range not smaller than +−1 mm (total range 2 mm), preferably not smaller than +−1.5 mm (total range 3 mm). Thereby, the smallest detectable displacement with a 4 mm long magnet is not larger than 10 micrometer, preferably not larger than 5 micrometer. In an alternative embodiment, the length of the magnet is increased, yielding a further increased range.

Example 8: Example with Hall Sensor Array

In this example embodiment, the sensor of the integrated device comprises a Hall sensor array comprising a plurality of Hall sensors, whereby said piece of ferromagnetic material comprises a plurality of magnetic pole pairs. In a preferred embodiment, this concerns an NSE-5310.

The invention claimed is:

1. An integrated device suitable for measuring a difference between a strain in a ligament at a first point in time and said strain at a second point in time, said integrated device comprising
   a ligament-attaching element adapted to be fastened on said ligament;
   a slider module adapted to be fastened on said ligament near said ligament-attaching element, said slider module comprising a slider guiding channel;
   a slider comprising a distal slider end and a proximal slider end, said distal slider end fastened on said ligament-attaching element, said proximal slider end guided in said slider guiding channel;
   a sensor configured to measure a strain-indicating parameter representing a position of said proximal slider end for obtaining said difference between said strain in said ligament at said first point in time and said strain at said second point in time, wherein said sensor comprises a Hall sensor, which converts a position of said proximal slider end into a conditioned electrical signal carrying said measurement of said strain-indicating parameter, whereby said slider comprises an elongated strip and/or wire comprising a non-magnetic material with low deformation under tensile stress and/or compressive stress and/or bending.

2. The integrated device according to claim 1, whereby said sensor comprises two or more Hall sensors, for robust measurement, said two or more Hall sensors placed in close proximity.

3. The integrated device according to claim 1, whereby said slider module comprises a slider module length, a slider module width and a slider module height; whereby either of said slider module length and said slider module width is not larger than 18 mm whereby said slider module height is not larger than 8 mm, and whereby said slider is not longer than 30 mm.

4. The integrated device according to claim 1, whereby said ligament-attaching element and said slider module are adapted to be fastened on said ligament by sewing.

5. The integrated device according to claim 1, whereby said ligament-attaching element and said slider module are adapted to be fastened on said ligament by any or any combination of the following: dry glue; micro needles.

6. The integrated device according to claim 1, said integrated device further comprising a transmitter module, said transmitter module configured to transmit said measurement of said strain-indicating parameter to a computer device, and whereby said integrated device comprises a power source, whereby said integrated device is adapted to operate entirely within a sterile zone in close proximity to said ligament, without any cable going beyond said sterile zone.

7. The integrated device according to claim 6, whereby said transmitter module comprises an integrated sensing module for measuring a sensing parameter, said transmitter module configured to transmit said measurement of said sensing parameter to said computer device, and whereby said integrated sensing module comprises any or any of the following: an accelerometer; a gyroscope; a magnetometer; a positioning meter.

8. The integrated device according to claim 6, whereby said ligament-attaching element and said slider module are adapted to be attached to said ligament belonging to a knee belonging to a leg of a patient, and whereby said transmitter module is adapted to be attached to a tibia belonging to said leg of said patient.

9. The integrated device according to claim 1, whereby said integrated device is adapted to be sterilized, said integrated device comprising an OFF-mode for preventing battery drain during storage and battery-relating damage to said integrated device due to sterilizing.

10. A kit comprising
   the integrated device according to claim 1;
   a knee prosthesis adapted for total knee arthroplasty.

11. An integrated device suitable for measuring a difference between a strain in a ligament at a first point in time and said strain at a second point in time, said integrated device comprising:
   a ligament-attaching element adapted to be fastened on said ligament;
   a slider module adapted to be fastened on said ligament near said ligament-attaching element, said slider module comprising a slider guiding channel;
   a slider comprising a distal slider end and a proximal slider end, said distal slider end fastened on said ligament-attaching element, said proximal slider end guided in said slider guiding channel;
   a sensor configured to measure a strain-indicating parameter representing a position of said proximal slider end for obtaining said difference between said strain in said ligament at said first point in time and said strain at said second point in time, wherein said sensor comprises a Hall sensor, which converts a position of said proximal slider end into a conditioned electrical signal carrying said measurement of said strain-indicating parameter, wherein said slider module comprises a slider housing and a slider head; said slider housing comprising said slider guiding channel and said sensor; said slider head comprising a piece of ferromagnetic material comprising at least one magnetic pole pair; wherein said slider head and said slider housing are adapted for sliding of said slider head within said slider housing, wherein said proximal slider end is attached to said slider head, and wherein said Hall sensor is configured for converting a position of said piece of ferromagnetic material into said measurement of said strain-indicating parameter.

12. The integrated device according to claim 11, whereby said sensor comprises said two or more Hall sensors configured such that said sensor is sensitive to a magnetic field variation along a single axis only, said single axis coinciding with a path of said piece of ferromagnetic material during said sliding.

13. The integrated device according to claim 11, whereby said sensor comprises a Hall sensor array comprising a plurality of Hall sensors, and whereby said piece of ferromagnetic material comprises a plurality of magnetic pole pairs.

14. A kit comprising:
the integrated device according to claim 11;
a knee prosthesis adapted for total knee arthroplasty.

15. An integrated system suitable for positioning of a knee prosthesis of a patient, said system comprising an integrated device suitable for measuring a difference between a strain in a ligament at a first point in time and said strain at a second point in time, said integrated device comprising:
- a ligament-attaching element adapted to be fastened on said ligament;
- a slider module adapted to be fastened on said ligament near said ligament-attaching element, said slider module comprising a slider guiding channel;
- a slider comprising a distal slider end and a proximal slider end, said distal slider end fastened on said ligament-attaching element, said proximal slider end guided in said slider guiding channel;
- a sensor configured to measure a strain-indicating parameter representing a position of said proximal slider end for obtaining said difference between said strain in said ligament at said first point in time and strain at said second point in time, wherein said sensor comprises a Hall sensor, which converts a position of said proximal slider end into a conditioned electrical signal carrying said measurement of said strain-indicating parameter;
- a computer device comprising a processor; tangible, non-transitory memory; program code on said memory instructing said processor;
- wherein said computer device is configured to receive a measurement of a strain-indicating parameter and/or a measurement of a sensing parameter, wherein said computer is configured to process said measurement of said strain-indicating parameter and/or said measurement of said sensing parameter, including any or any combination of the following: calculation of a statistical quantity relating to said strain-indicating parameter and/or said sensing parameter, visualization of a diagram relating to said strain-indicating parameter and/or said sensing parameter, configuration of a system parameter relating to said sensor and/or an integrated sensing module, derivation of a flexion of said knee of said patient from said measurement of said sensing parameter;
- wherein said computer device is configured for computing a difference between a strain in a ligament at a first point in time and said strain at a second point in time, whereby said first point in time precedes application of said knee prosthesis of said patient, and whereby said second point in time occurs simultaneously with said application of said knee prosthesis, said difference thereby being indicative of the positioning of said knee prosthesis.

16. A computer program product for use in a computer device belonging to the integrated system according to claim 15, said computer program product including a plurality of computer executable instructions stored on a computer readable medium, wherein said instructions, when executed by said computer device, cause the computer device to perform the steps of:
- (01) receiving a first measurement of said strain-indicating parameter and/or a measurement of said sensing parameter from said integrated device;
- (02) receiving a second measurement of said strain-indicating parameter and/or a measurement of said sensing parameter from said integrated device,
- (03) computing a difference between said first and said second measurement of said strain-indicating parameter and/or said measurement of said sensing parameter including any or any combination of the following: calculation of a statistical quantity relating to said strain-indicating parameter and/or said sensing parameter, visualization of a diagram relating to said strain-indicating parameter and/or said sensing parameter, configuration of a system parameter relating to said sensor and/or said integrated sensing module, derivation of a flexion of a knee of a patient from said measurement of said sensing parameter,
- (04) communicating a result of step (03) relating to said strain-indicating parameter and/or said sensing parameter.

* * * * *